United States Patent
Wu et al.

(10) Patent No.: US 12,274,264 B2
(45) Date of Patent: Apr. 15, 2025

(54) PIPERONYLIC ACID DERIVATIVE AND APPLICATION THEREOF

(71) Applicants: SHENYANG SINOCHEM AGROCHEMICALS R&D CO., LTD., Liaoning (CN); Jiangsu Yangnong Chemical Co., Ltd., Jiangsu (CN)

(72) Inventors: Hongfei Wu, Liaoning (CN); Jingbo Xu, Liaoning (CN); Shaowu Liu, Liaoning (CN); Haibo Yu, Liaoning (CN); Lanfeng Ban, Liaoning (CN); Libao Xu, Liaoning (CN); Xueming Cheng, Liaoning (CN); Chunxiao Guo, Liaoning (CN); Ningning Sun, Liaoning (CN)

(73) Assignees: SHENYANG SINOCHEM AGROCHEMICALS R&D CO., LTD, Shenyang (CN); JIANGSU YANGNONG CHEMICAL CO., LTD, Jiangsu (CN)

( * ) Notice: Subject to any disclaimer, the term of this patent is extended or adjusted under 35 U.S.C. 154(b) by 620 days.

(21) Appl. No.: 17/687,385

(22) Filed: Mar. 4, 2022

(65) Prior Publication Data
US 2022/0202011 A1     Jun. 30, 2022

Related U.S. Application Data

(63) Continuation-in-part of application No. PCT/CN2020/112749, filed on Sep. 1, 2020.

(30) Foreign Application Priority Data

Sep. 6, 2019   (CN) .................. 201910842263.X

(51) Int. Cl.
  *C07D 317/46*   (2006.01)
  *A01N 43/30*    (2006.01)
  *A01P 7/04*     (2006.01)

(52) U.S. Cl.
  CPC ............... *A01N 43/30* (2013.01); *A01P 7/04* (2021.08); *C07D 317/46* (2013.01)

(58) Field of Classification Search
  CPC ................................................ C07D 317/46
  See application file for complete search history.

(56) References Cited

U.S. PATENT DOCUMENTS

| 8,853,440 B2 | 10/2014 | Aoki et al. |
| 9,839,216 B2 * | 12/2017 | Pitterna .................. A01N 43/40 |
| 2011/0137068 A1 | 6/2011 | Aoki et al. |

FOREIGN PATENT DOCUMENTS

| CN | 101203132 A | 6/2008 |
| CN | 105873901 A | 8/2016 |
| CN | 109206397 A | 1/2019 |

OTHER PUBLICATIONS

Toshifumi Nakao et al., "Broflanilide: A meta-diamide insecticide with a novel mode of action", Bioorganic & Medicinal Chemistry, vol. 24, Aug. 28, 2015, pp. 372-377.

* cited by examiner

*Primary Examiner* — Golam M Shameem
(74) *Attorney, Agent, or Firm* — NKL Law; Allen Xue

(57) ABSTRACT

The present invention belongs to the fields of insecticides and acaricides, and particularly relates to a piperonylic acid derivative and application thereof. The structure is shown in a general formula I, and the definition of each substituent in the formula is described in the description. The compound of the general formula I has excellent insecticidal and acaricidal activity and can be used for controlling various pests and mites.

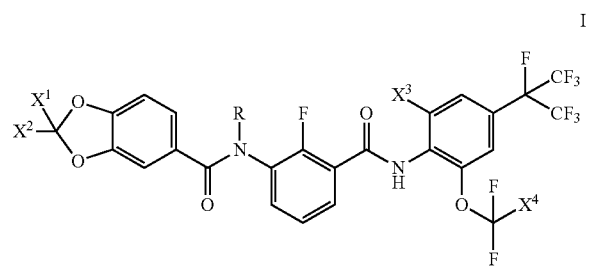

7 Claims, No Drawings

PIPERONYLIC ACID DERIVATIVE AND APPLICATION THEREOF

TECHNICAL FIELD

The present invention belongs to the fields of insecticides and acaricides, and particularly relates to a piperonylic acid derivative and application thereof.

BACKGROUND

Corresponding control objects will be resistant to the insecticides or acaricides which are used for a period of time. Therefore, insecticides or acaricides and compositions thereof with better activity and lower dosage need to be continuously developed.

CN109206397 discloses piperonylic acid derivatives $KC_1$ (compound number in the patent: compound I-8) and $KC_2$ (compound number in the patent: compound I-51), and insecticidal and acaricidal activities thereof.

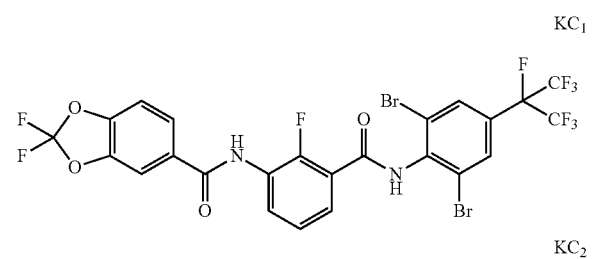

U.S. Pat. No. 8,853,440B2 discloses that a compound $KC_3$ (Pesticide common name: Broflanilide, compound number in the patent: compound 3-1) shows activities greater than or equal to 70% against *Spodoptera litura* and *Plutella xylostella* at a concentration of 1 ppm.

U.S. Pat. No. 9,839,216B2 discloses that a compound $KC_4$ (compound number in the patent: compound 31) shows activities greater than or equal to 80% against *Plutella xylostella*, *Spodoptera littoralis*, *Tetranychus urticae* koch and trips tabaci at a concentration of 200 ppm. The scope of claims in the patent description also includes unlisted compounds, i.e., the compound MC, the methylated $KC_4$.

These disclosed compounds show insecticidal or acaricidal activity, but the insecticidal effect is not ideal at low doses. In this field, new insecticides with high insecticidal activity at low doses still need to be actively developed to satisfy the needs of agriculture, forestry or health field.

In the present invention, the compound of the general formula I is obtained by introducing piperonylic acid natural active molecules and specially substituted 4-heptafluoroisopropyl aniline active substructure, and unexpected biological activity results are obtained. The piperonylic acid derivative shown in the present invention and the insecticidal and acaricidal activities have not been reported.

SUMMARY

Aiming at the defects of the prior art, the purpose of the present invention is to provide a new piperonylic acid derivative, and application thereof as an insecticide and an acaricide. The compound can have good insecticidal and acaricidal effects under low dosage.

To achieve the above purpose, the present invention adopts the following technical solution:

A piperonylic acid derivative is shown in a general formula I:

Wherein:
$X^1$ is selected from halogens;
$X^2$ is selected from H or halogens;
$X^3$ is selected from halogens or $C_1$-$C_3$ haloalkyl;
$X^4$ is selected from H or halogens;
R is selected from H, $C_1$-$C_6$ alkyl, $C_1$-$C_6$ haloalkyl, $C_2$-$C_{10}$ alkenyl, $C_1$-$C_6$ alkoxy $C_1$-$C_6$ alkyl or $C_1$-$C_6$ alkylthio $C_1$-$C_6$ alkyl.

A preferred compound in the present invention is: in the general formula I $X^1$ is selected from F, Cl or Br;

$X^2$ is selected from H, F, Cl or Br;

$X^3$ is selected from F, Cl, Br, I or halomethyl;

$X^4$ is selected from H, F, Cl or Br;

R is selected from H, $C_1$-$C_6$ alkyl, $C_1$-$C_6$ haloalkyl, $C_2$-$C_{10}$ alkenyl, $C_1$-$C_6$ alkoxy $C_1$-$C_6$ alkyl or $C_1$-$C_6$ alkylthio $C_1$-$C_6$ alkyl.

A further preferred compound in the present invention is: in the general formula I $X^1$ is selected from F;

$X^2$ is selected from H or F.

$X^3$ is selected from F, Cl, Br, I or halomethyl;

$X^4$ is selected from H, F, Cl or Br;

R is selected from H, $C_1$-$C_6$ alkyl, $C_1$-$C_6$ haloalkyl, $C_2$-$C_{10}$ alkenyl, $C_1$-$C_6$ alkoxy $C_1$-$C_6$ alkyl or $C_1$-$C_6$ alkylthio $C_1$-$C_6$ alkyl.

A further preferred compound in the present invention is: in the formula I $X^1$ is selected from F;

$X^2$ is selected from H or F.

$X^3$ is selected from F, Cl, Br, I or halomethyl;

$X^4$ is selected from H or F.

R is selected from H, $C_1$-$C_6$ alkyl, $C_1$-$C_6$ haloalkyl, $C_2$-$C_{10}$ alkenyl, $C_1$-$C_6$ alkoxy $C_1$-$C_6$ alkyl or $C_1$-$C_6$ alkylthio $C_1$-$C_6$ alkyl.

A further preferred compound in the present invention is: in the general formula I $X^1$ is selected from F;

$X^2$ is selected from H or F.

$X^3$ is selected from F, Cl, Br, I or halomethyl;

$X^4$ is selected from H or F.

R is selected from H, $C_1$-$C_6$ alkyl or methylthiopropyl.

The compound of the formula I in the present invention can be prepared by the methods in CN109206397. Unless otherwise stated, the definitions of the groups in the formula are the same as above.

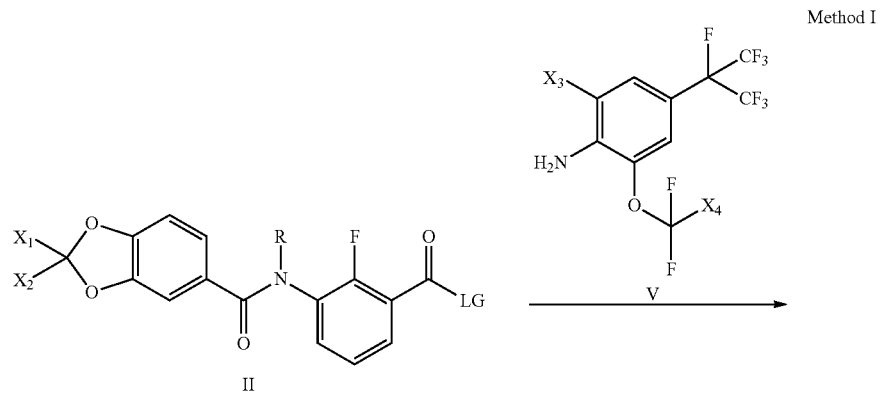

Method I

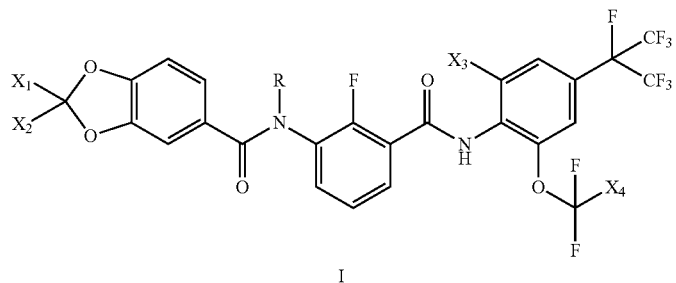

I

In the formula, LG in the compound of the general formula II is a leaving group such as E ($C_1$-$C_6$ alkoxyl) in the general formula II-a, OH in the general formula II-b or M (halogen) in the general formula II-c in the following formula. A specific synthesis method is as follows:

erated with a proper acyl halide reagent (such as oxalyl chloride, thionyl chloride, phosphorus tribromide and phosphorus oxybromide) to prepare the compound (substituted benzoyl halide) of the general formula II-c, and the compound (substituted aniline) of the general formula V is

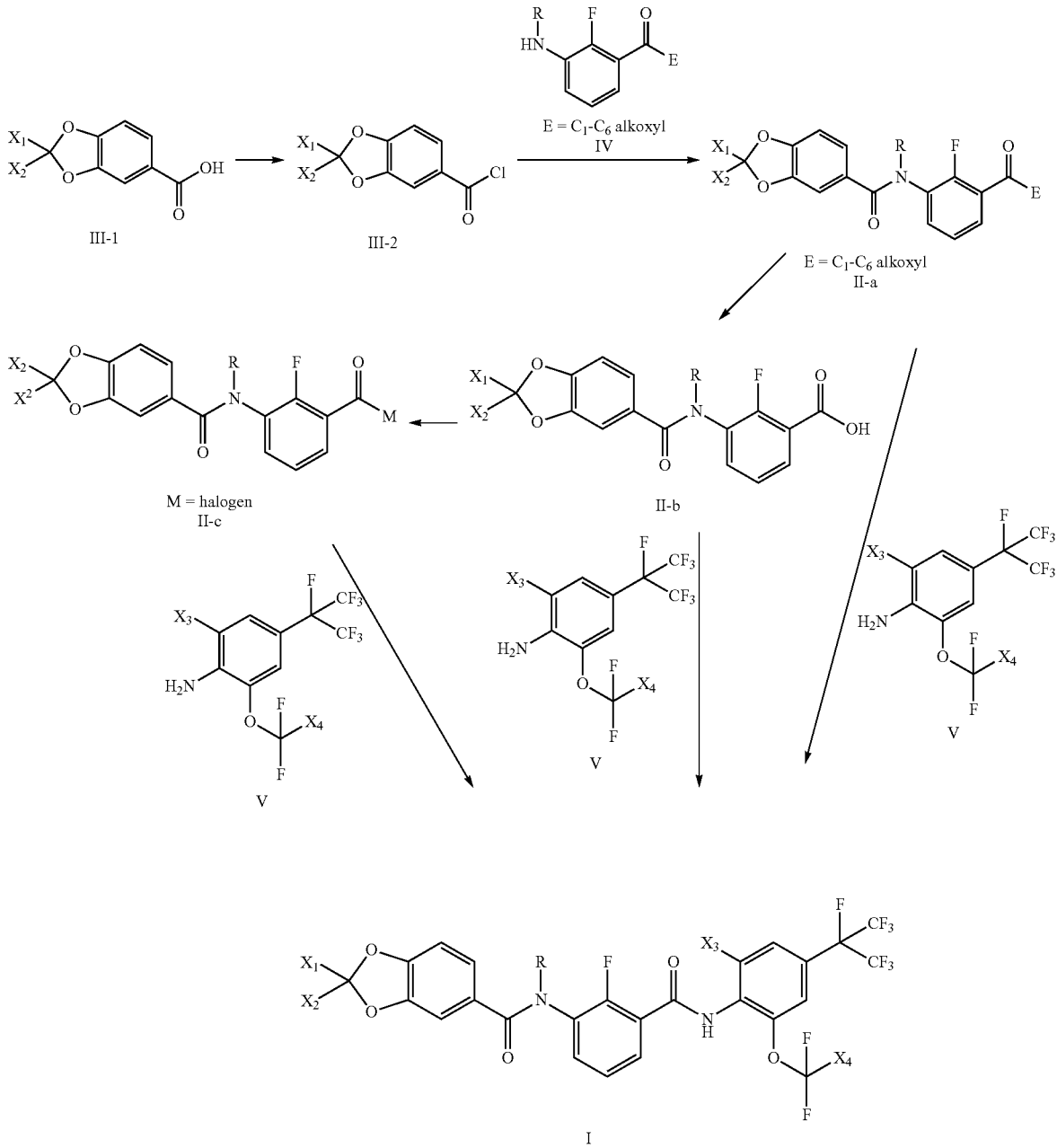

The compound of the general formula III-1 is acyl chlorinated with a proper acyl chloride reagent (such as oxalyl chloride and thionyl chloride) to prepare acyl chloride III-2, and the compound (substituted aniline) of the general formula IV is converted into the compound of the general formula II-a by acylation with acyl chloride III-2. The compound (substituted benzoate) of the general formula II-a is hydrolyzed to obtain the compound (substituted benzoic acid) of the general formula II-b. The compound (substituted benzoic acid) of the general formula IT-b is acyl halogen-converted into the compound of the general formula I by acylation with acyl halide the compound of the general formula II-c.

Or, the compound of the general formula II-a is converted into the compound of the general formula I by ammonolysis reaction with the compound of the general formula V.

Or, the compound of the general formula II-b is converted into the compound of the general formula I by condensation reaction with the compound of the general formula V.

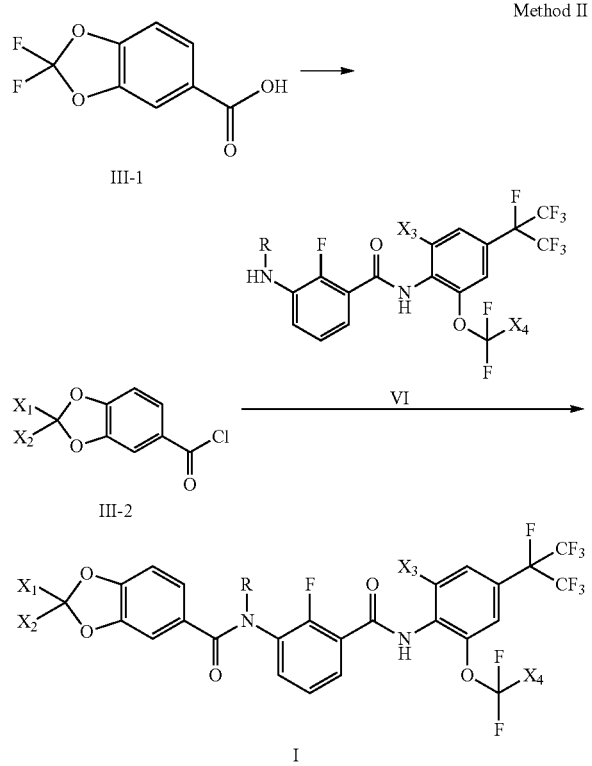

The compound of the general formula III-1 is acyl chlorinated with a proper acyl chloride reagent (such as oxalyl chloride and thionyl chloride) to prepare acyl chloride III-2, and the compound (substituted aniline) of the general formula VI is converted into the compound of the general formula I by acylation with acyl chloride III-2.

In the definitions of the compounds of the general formulas provided above, the terms used in the collection generally represent the following substituents:

Halogen: F, Cl, Br or I.

Alkyl: linear, branched or cyclic alkyl, such as methyl, ethyl, n-propyl, isopropyl or cyclopropyl.

Alkenyl: linear, branched or cyclic alkenyl, such as vinyl, 1-propenyl, 2-propenyl and different butenyl, pentenyl and hexenyl isomers. The alkenyl also comprises polyenes, such as 1,2-propadienyl and 2,4-hexadienyl.

Haloalkyl: linear, branched or cyclic alkyl on which hydrogen atoms can be partially or fully replaced by the halogens, such as chloromethyl, dichloromethyl, trichloromethyl, fluoromethyl, difluoromethyl, trifluoromethyl, pentafluoroethyl or heptafluoroisopropyl.

Alkoxyl: linear, branched or cyclic alkoxyl, such as methoxyl, ethoxyl, n-propoxyl, isopropoxyl, cyclopropyloxyl or n-butoxyl.

Alkylthio: linear, branched or cyclic alkylthio, such as methylthio, ethylthio, n-propylthio, isopropylthio, cyclopropylthio or n-butylthio.

The sources of raw materials and intermediates involved in the above preparation method are as follows:

Intermediate IV, intermediate V and intermediate VI can be prepared according to the methods in U.S. Pat. No. 8,853,440B2 and U.S. Pat. No. 9,839,216B2.

Intermediate III-1, the acyl halide reagent, and other conventional raw materials and reagents are generally commercially available or can be prepared according to a conventional method.

In the compounds of the present invention, the compound of the general formula I is a chirality structural compound due to the difference between $X^1$ and $X^2$. In this case, the compounds may exist in a form of a single chirality isomer or a mixture of two chirality isomers. The compound shown in the general formula I as claimed by the present invention is not limited by the existence form of the above isomer structures.

The specific compounds listed in Table 1 can be used to illustrate the present invention, but not to limit the present invention.

TABLE 1

| No. | $X^1$ | $X^2$ | $X^3$ | $X^4$ | R |
|---|---|---|---|---|---|
| I-1 | F | F | I | H | H |
| I-2 | F | F | I | H | —CH$_3$ |
| I-3 | F | F | I | H | —CH$_2$CH$_3$ |
| I-4 | F | F | I | H | —CH$_2$CH$_2$CH$_3$ |
| I-5 | F | F | I | H | —CH(CH$_3$)$_2$ |
| I-6 | F | F | I | H | —CH$_2$CH$_2$CH$_2$CH$_3$ |
| I-7 | F | F | I | H | —CH$_2$CH(CH$_3$)$_2$ |
| I-8 | F | F | I | H | —CH(CH$_3$)(CH$_2$CH$_3$) |
| I-9 | F | F | I | H | —C(CH$_3$)$_3$ |
| I-10 | F | F | I | H | cyclopropylmethyl |
| I-11 | F | F | I | H | —CH$_2$CH$_2$CH$_2$CH$_2$CH$_3$ |
| I-12 | F | F | I | H | —CH$_2$C(CH$_3$)$_3$ |
| I-13 | F | F | I | H | —CH$_2$CF$_3$ |
| I-14 | F | F | I | H | —CH$_2$CH$_2$CF$_3$ |
| I-15 | F | F | I | H | allyl |
| I-16 | F | F | I | H | but-3-enyl |
| I-17 | F | F | I | H | geranyl |
| I-18 | F | F | I | H | farnesyl-type |
| I-19 | F | F | I | H | —CH$_2$CH$_2$CH$_2$OCH$_3$ |
| I-20 | F | F | I | H | —CH$_2$CH$_2$CH$_2$SCH$_3$ |

TABLE 1-continued

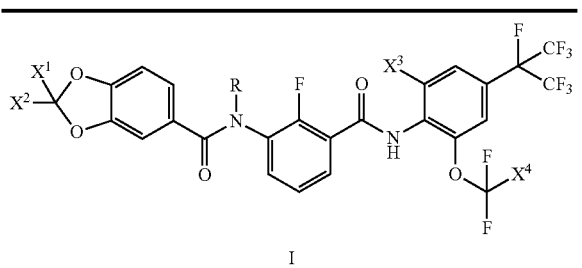

I

| No. | X¹ | X² | X³ | X⁴ | R |
|---|---|---|---|---|---|
| I-21 | F | F | I | F | H |
| I-22 | F | F | I | F | —CH₃ |
| I-23 | F | F | I | F | —CH₂CH₃ |
| I-24 | F | F | I | F | —CH₂CH₂CH₃ |
| I-25 | F | F | I | F | —CH(CH₃)₂ |
| I-26 | F | F | I | F | —CH₂CH₂CH₂CH₃ |
| I-27 | F | F | I | F | —CH₂CH(CH₃)₂ |
| I-28 | F | F | I | F | —CH(CH₃)(CH₂CH₃) |
| I-29 | F | F | I | F | —C(CH₃)₃ |
| I-30 | F | F | I | F | (cyclopropylmethyl) |
| I-31 | F | F | I | F | —CH₂CH₂CH₂CH₂CH₃ |
| I-32 | F | F | I | F | —CH₂C(CH₃)₃ |
| I-33 | F | F | I | F | —CH₂CF₃ |
| I-34 | F | F | I | F | —CH₂CH₂CF₃ |
| I-35 | F | F | I | F | (allyl-type) |
| I-36 | F | F | I | F | (pentenyl) |
| I-37 | F | F | I | F | (citronellyl) |
| I-38 | F | F | I | F | (geranyl) |
| I-39 | F | F | I | F | (methoxypropyl) |
| I-40 | F | F | I | F | (methylthiopropyl) |
| I-41 | F | F | Br | H | H |
| I-42 | F | F | Br | H | —CH₃ |
| I-43 | F | F | Br | H | —CH₂CH₃ |
| I-44 | F | F | Br | H | —CH₂CH₂CH₃ |
| I-45 | F | F | Br | H | —CH(CH₃)₂ |
| I-46 | F | F | Br | H | —CH₂CH₂CH₂CH₃ |
| I-47 | F | F | Br | H | —CH₂CH(CH₃)₂ |
| I-48 | F | F | Br | H | —CH(CH₃)(CH₂CH₃) |
| I-49 | F | F | Br | H | —C(CH₃)₃ |
| I-50 | F | F | Br | H | (cyclopropylmethyl) |
| I-51 | F | F | Br | H | —CH₂CH₂CH₂CH₂CH₃ |
| I-52 | F | F | Br | H | —CH₂C(CH₃)₃ |
| I-53 | F | F | Br | H | —CH₂CF₃ |
| I-54 | F | F | Br | H | —CH₂CH₂CF₃ |
| I-55 | F | F | Br | H | (allyl-type) |
| I-56 | F | F | Br | H | (pentenyl) |
| I-57 | F | F | Br | H | (citronellyl) |
| I-58 | F | F | Br | H | (geranyl) |
| I-59 | F | F | Br | H | (methoxypropyl) |
| I-60 | F | F | Br | H | (methylthiopropyl) |
| I-61 | F | F | Br | F | H |
| I-62 | F | F | Br | F | —CH₃ |
| I-63 | F | F | Br | F | —CH₂CH₃ |
| I-64 | F | F | Br | F | —CH₂CH₂CH₃ |
| I-65 | F | F | Br | F | —CH(CH₃)₂ |
| I-66 | F | F | Br | F | —CH₂CH₂CH₂CH₃ |
| I-67 | F | F | Br | F | —CH₂CH(CH₃)₂ |
| I-68 | F | F | Br | F | —CH(CH₃)(CH₂CH₃) |
| I-69 | F | F | Br | F | —C(CH₃)₃ |
| I-70 | F | F | Br | F | (cyclopropylmethyl) |
| I-71 | F | F | Br | F | —CH₂CH₂CH₂CH₂CH₃ |
| I-72 | F | F | Br | F | —CH₂C(CH₃)₃ |
| I-73 | F | F | Br | F | —CH₂CF₃ |
| I-74 | F | F | Br | F | —CH₂CH₂CF₃ |
| I-75 | F | F | Br | F | (allyl-type) |

TABLE 1-continued

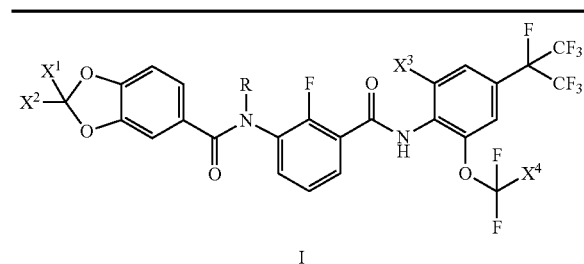

I

| No. | X¹ | X² | X³ | X⁴ | R |
|---|---|---|---|---|---|
| I-76 | F | F | Br | F | 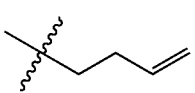 [SMILES: *CCC=C] |
| I-77 | F | F | Br | F | 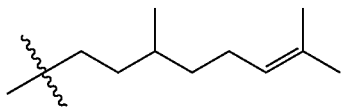 [SMILES: *CCC(C)CCC=C(C)C] |
| I-78 | F | F | Br | F | 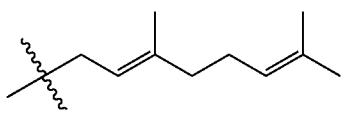 [SMILES: *C/C=C(\C)CCC=C(C)C] |
| I-79 | F | F | Br | F | 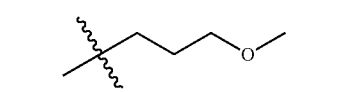 [SMILES: *CCCOC] |
| I-80 | F | F | Br | F | 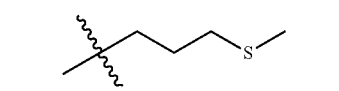 [SMILES: *CCCSC] |
| I-81 | F | F | Cl | H | H |
| I-82 | F | F | Cl | H | —CH₃ |
| I-83 | F | F | Cl | H | —CH₂CH₃ |
| I-84 | F | F | Cl | H | —CH₂CH₂CH₃ |
| I-85 | F | F | Cl | H | —CH(CH₃)₂ |
| I-86 | F | F | Cl | H | —CH₂CH₂CH₂CH₃ |
| I-87 | F | F | Cl | H | —CH₂CH(CH₃)₂ |
| I-88 | F | F | Cl | H | —CH(CH₃)(CH₂CH₃) |
| I-89 | F | F | Cl | H | —C(CH₃)₃ |
| I-90 | F | F | Cl | H |  |
| I-91 | F | F | Cl | H | —CH₂CH₂CH₂CH₂CH₃ |
| I-92 | F | F | Cl | H | —CH₂C(CH₃)₃ |
| I-93 | F | F | Cl | H | —CH₂CF₃ |
| I-94 | F | F | Cl | H | —CH₂CH₂CF₃ |
| I-95 | F | F | Cl | H |  |
| I-96 | F | F | Cl | H | 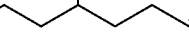 |
| I-97 | F | F | Cl | H |  |

TABLE 1-continued

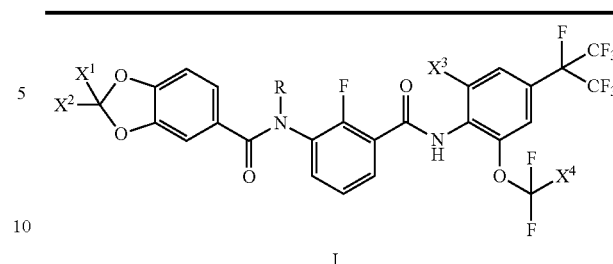

I

| No. | X¹ | X² | X³ | X⁴ | R |
|---|---|---|---|---|---|
| I-98 | F | F | Cl | H | 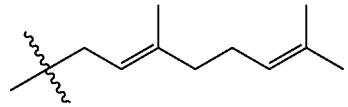 [SMILES: *C/C=C(\C)CCC=C(C)C] |
| I-99 | F | F | Cl | H | 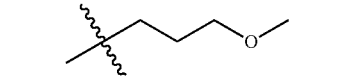 [SMILES: *CCCOC] |
| I-100 | F | F | Cl | H | 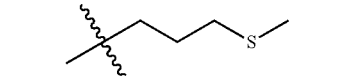 [SMILES: *CCCSC] |
| I-101 | F | F | Cl | F | H |
| I-102 | F | F | Cl | F | —CH₃ |
| I-103 | F | F | Cl | F | —CH₂CH₃ |
| I-104 | F | F | Cl | F | —CH₂CH₂CH₃ |
| I-105 | F | F | Cl | F | —CH(CH₃)₂ |
| I-106 | F | F | Cl | F | —CH₂CH₂CH₂CH₃ |
| I-107 | F | F | Cl | F | —CH₂CH(CH₃)₂ |
| I-108 | F | F | Cl | F | —CH(CH₃)(CH₂CH₃) |
| I-109 | F | F | Cl | F | —C(CH₃)₃ |
| I-110 | F | F | Cl | F |  |
| I-111 | F | F | Cl | F | —CH₂CH₂CH₂CH₂CH₃ |
| I-112 | F | F | Cl | F | —CH₂C(CH₃)₃ |
| I-113 | F | F | Cl | F | —CH₂CF₃ |
| I-114 | F | F | Cl | F | —CH₂CH₂CF₃ |
| I-115 | F | F | Cl | F |  |
| I-116 | F | F | Cl | F |  |
| I-117 | F | F | Cl | F |  |
| I-118 | F | F | Cl | F |  |
| I-119 | F | F | Cl | F |  |

TABLE 1-continued

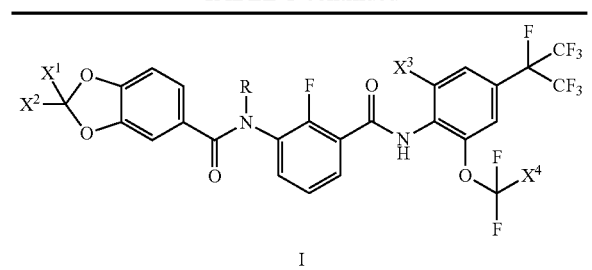

I

| No. | X¹ | X² | X³ | X⁴ | R |
|---|---|---|---|---|---|
| I-120 | F | F | Cl | F | |
| I-121 | F | F | CF₃ | H | H |
| I-122 | F | F | CF₃ | H | —CH₃ |
| I-123 | F | F | CF₃ | H | —CH₂CH₃ |
| I-124 | F | F | CF₃ | H | —CH₂CH₂CH₃ |
| I-125 | F | F | CF₃ | H | —CH(CH₃)₂ |
| I-126 | F | F | CF₃ | H | —CH₂CH₂CH₂CH₃ |
| I-127 | F | F | CF₃ | H | —CH₂CH(CH₃)₂ |
| I-128 | F | F | CF₃ | H | —CH(CH₃)(CH₂CH₃) |
| I-129 | F | F | CF₃ | H | —C(CH₃)₃ |
| I-130 | F | F | CF₃ | H | (CH₂-cyclopropyl) |
| I-131 | F | F | CF₃ | H | —CH₂CH₂CH₂CH₂CH₃ |
| I-132 | F | F | CF₃ | H | —CH₂C(CH₃)₃ |
| I-133 | F | F | CF₃ | H | —CH₂CF₃ |
| I-134 | F | F | CF₃ | H | —CH₂CH₂CF₃ |
| I-135 | F | F | CF₃ | H | (allyl) |
| I-136 | F | F | CF₃ | H | (butenyl) |
| I-137 | F | F | CF₃ | H | (citronellyl) |
| I-138 | F | F | CF₃ | H | (geranyl) |
| I-139 | F | F | CF₃ | H | (CH₂CH₂CH₂OCH₃) |
| I-140 | F | F | CF₃ | H | (CH₂CH₂CH₂SCH₃) |
| I-141 | F | F | CF₃ | F | H |
| I-142 | F | F | CF₃ | F | —CH₃ |
| I-143 | F | F | CF₃ | F | —CH₂CH₃ |
| I-144 | F | F | CF₃ | F | —CH₂CH₂CH₃ |
| I-145 | F | F | CF₃ | F | —CH(CH₃)₂ |
| I-146 | F | F | CF₃ | F | —CH₂CH₂CH₂CH₃ |
| I-147 | F | F | CF₃ | F | —CH₂CH(CH₃)₂ |
| I-148 | F | F | CF₃ | F | —CH(CH₃)(CH₂CH₃) |
| I-149 | F | F | CF₃ | F | —C(CH₃)₃ |
| I-150 | F | F | CF₃ | F | (CH₂-cyclopropyl) |
| I-151 | F | F | CF₃ | F | —CH₂CH₂CH₂CH₂CH₃ |
| I-152 | F | F | CF₃ | F | —CH₂C(CH₃)₃ |
| I-153 | F | F | CF₃ | F | —CH₂CF₃ |
| I-154 | F | F | CF₃ | F | —CH₂CH₂CF₃ |
| I-155 | F | F | CF₃ | F | (allyl) |
| I-156 | F | F | CF₃ | F | (butenyl) |
| I-157 | F | F | CF₃ | F | (citronellyl) |
| I-158 | F | F | CF₃ | F | (geranyl) |
| I-159 | F | F | CF₃ | F | (CH₂CH₂CH₂OCH₃) |
| I-160 | F | F | CF₃ | F | (CH₂CH₂CH₂SCH₃) |
| I-161 | Cl | Cl | I | H | H |
| I-162 | Cl | Cl | I | H | —CH₃ |
| I-163 | Cl | Cl | I | H | —CH₂CH₃ |
| I-164 | Cl | Cl | I | H | —CH₂CH₂CH₃ |
| I-165 | Cl | Cl | I | H | —CH(CH₃)₂ |
| I-166 | Cl | Cl | I | H | —CH₂CH₂CH₂CH₃ |
| I-167 | Cl | Cl | I | H | —CH₂CH(CH₃)₂ |
| I-168 | Cl | Cl | I | H | —CH(CH₃)(CH₂CH₃) |
| I-169 | Cl | Cl | I | H | —C(CH₃)₃ |
| I-170 | Cl | Cl | I | H | (CH₂-cyclopropyl) |
| I-171 | Cl | Cl | I | H | —CH₂CH₂CH₂CH₂CH₃ |
| I-172 | Cl | Cl | I | H | —CH₂C(CH₃)₃ |
| I-173 | Cl | Cl | I | H | —CH₂CF₃ |
| I-174 | Cl | Cl | I | H | —CH₂CH₂CF₃ |

TABLE 1-continued

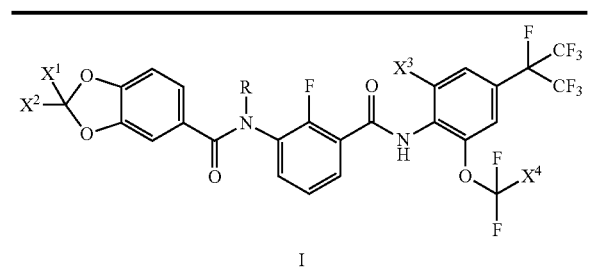

I

| No. | X¹ | X² | X³ | X⁴ | R |
|---|---|---|---|---|---|
| I-175 | Cl | Cl | I | H | (but-3-enyl, branched) |
| I-176 | Cl | Cl | I | H | (pent-4-enyl) |
| I-177 | Cl | Cl | I | H | (citronellyl-type) |
| I-178 | Cl | Cl | I | H | (geranyl-type) |
| I-179 | Cl | Cl | I | H | (−CH₂CH₂CH₂OCH₃) |
| I-180 | Cl | Cl | I | H | (−CH₂CH₂CH₂SCH₃) |
| I-181 | Cl | Cl | I | F | H |
| I-182 | Cl | Cl | I | F | —CH₃ |
| I-183 | Cl | Cl | I | F | —CH₂CH₃ |
| I-184 | Cl | Cl | I | F | —CH₂CH₂CH₃ |
| I-185 | Cl | Cl | I | F | —CH(CH₃)₂ |
| I-186 | Cl | Cl | I | F | —CH₂CH₂CH₂CH₃ |
| I-187 | Cl | Cl | I | F | —CH₂CH(CH₃)₂ |
| I-188 | Cl | Cl | I | F | —CH(CH₃)(CH₂CH₃) |
| I-189 | Cl | Cl | I | F | —C(CH₃)₃ |
| I-190 | Cl | Cl | I | F | (cyclopropylmethyl) |
| I-191 | Cl | Cl | I | F | —CH₂CH₂CH₂CH₂CH₃ |
| I-192 | Cl | Cl | I | F | —CH₂C(CH₃)₃ |
| I-193 | Cl | Cl | I | F | —CH₂CF₃ |
| I-194 | Cl | Cl | I | F | —CH₂CH₂CF₃ |
| I-195 | Cl | Cl | I | F | (but-3-enyl) |
| I-196 | Cl | Cl | I | F | (pent-4-enyl) |

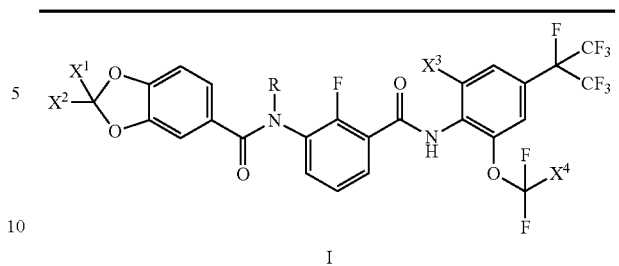

I

| No. | X¹ | X² | X³ | X⁴ | R |
|---|---|---|---|---|---|
| I-197 | Cl | Cl | I | F | (citronellyl-type) |
| I-198 | Cl | Cl | I | F | (geranyl-type) |
| I-199 | Cl | Cl | I | F | (−CH₂CH₂CH₂OCH₃) |
| I-200 | Cl | Cl | I | F | (−CH₂CH₂CH₂SCH₃) |
| I-201 | Cl | Cl | Br | H | H |
| I-202 | Cl | Cl | Br | H | —CH₃ |
| I-203 | Cl | Cl | Br | H | —CH₂CH₃ |
| I-204 | Cl | Cl | Br | H | —CH₂CH₂CH₃ |
| I-205 | Cl | Cl | Br | H | —CH(CH₃)₂ |
| I-206 | Cl | Cl | Br | H | —CH₂CH₂CH₂CH₃ |
| I-207 | Cl | Cl | Br | H | —CH₂CH(CH₃)₂ |
| I-208 | Cl | Cl | Br | H | —CH(CH₃)(CH₂CH₃) |
| I-209 | Cl | Cl | Br | H | —C(CH₃)₃ |
| I-210 | Cl | Cl | Br | H | (cyclopropylmethyl) |
| I-211 | Cl | Cl | Br | H | —CH₂CH₂CH₂CH₂CH₃ |
| I-212 | Cl | Cl | Br | H | —CH₂C(CH₃)₃ |
| I-213 | Cl | Cl | Br | H | —CH₂CF₃ |
| I-214 | Cl | Cl | Br | H | —CH₂CH₂CF₃ |
| I-215 | Cl | Cl | Br | H | (but-3-enyl) |
| I-216 | Cl | Cl | Br | H | (pent-4-enyl) |
| I-217 | Cl | Cl | Br | H | (citronellyl-type) |
| I-218 | Cl | Cl | Br | H | (geranyl-type) |

TABLE 1-continued

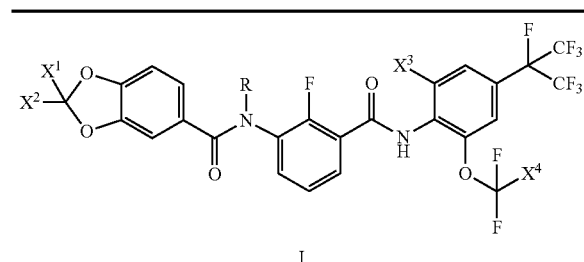

I

| No. | X¹ | X² | X³ | X⁴ | R |
|---|---|---|---|---|---|
| I-219 | Cl | Cl | Br | H | (3-methoxypropyl) |
| I-220 | Cl | Cl | Br | H | (3-(methylthio)propyl) |
| I-221 | Cl | Cl | Br | F | H |
| I-222 | Cl | Cl | Br | F | —CH₃ |
| I-223 | Cl | Cl | Br | F | —CH₂CH₃ |
| I-224 | Cl | Cl | Br | F | —CH₂CH₂CH₃ |
| I-225 | Cl | Cl | Br | F | —CH(CH₃)₂ |
| I-226 | Cl | Cl | Br | F | —CH₂CH₂CH₂CH₃ |
| I-227 | Cl | Cl | Br | F | —CH₂CH(CH₃)₂ |
| I-228 | Cl | Cl | Br | F | —CH(CH₃)(CH₂CH₃) |
| I-229 | Cl | Cl | Br | F | —C(CH₃)₃ |
| I-230 | Cl | Cl | Br | F | (cyclopropylmethyl) |
| I-231 | Cl | Cl | Br | F | —CH₂CH₂CH₂CH₂CH₃ |
| I-232 | Cl | Cl | Br | F | —CH₂C(CH₃)₃ |
| I-233 | Cl | Cl | Br | F | —CH₂CF₃ |
| I-234 | Cl | Cl | Br | F | —CH₂CH₂CF₃ |
| I-235 | Cl | Cl | Br | F | (allyl variant) |
| I-236 | Cl | Cl | Br | F | (butenyl) |
| I-237 | Cl | Cl | Br | F | (citronellyl) |
| I-238 | Cl | Cl | Br | F | (geranyl) |
| I-239 | Cl | Cl | Br | F | (3-methoxypropyl) |
| I-240 | Cl | Cl | Br | F | (3-(methylthio)propyl) |
| I-241 | Cl | Cl | Cl | H | H |
| I-242 | Cl | Cl | Cl | H | —CH₃ |
| I-243 | Cl | Cl | Cl | H | —CH₂CH₃ |
| I-244 | Cl | Cl | Cl | H | —CH₂CH₂CH₃ |
| I-245 | Cl | Cl | Cl | H | —CH(CH₃)₂ |
| I-246 | Cl | Cl | Cl | H | —CH₂CH₂CH₂CH₃ |
| I-247 | Cl | Cl | Cl | H | —CH₂CH(CH₃)₂ |
| I-248 | Cl | Cl | Cl | H | —CH(CH₃)(CH₂CH₃) |
| I-249 | Cl | Cl | Cl | H | —C(CH₃)₃ |
| I-250 | Cl | Cl | Cl | H | (cyclopropylmethyl) |
| I-251 | Cl | Cl | Cl | H | —CH₂CH₂CH₂CH₂CH₃ |
| I-252 | Cl | Cl | Cl | H | —CH₂C(CH₃)₃ |
| I-253 | Cl | Cl | Cl | H | —CH₂CF₃ |
| I-254 | Cl | Cl | Cl | H | —CH₂CH₂CF₃ |
| I-255 | Cl | Cl | Cl | H | (allyl variant) |
| I-256 | Cl | Cl | Cl | H | (butenyl) |
| I-257 | Cl | Cl | Cl | H | (citronellyl) |
| I-258 | Cl | Cl | Cl | H | (geranyl) |
| I-259 | Cl | Cl | Cl | H | (3-methoxypropyl) |
| I-260 | Cl | Cl | Cl | H | (3-(methylthio)propyl) |
| I-261 | Cl | Cl | Cl | F | H |
| I-262 | Cl | Cl | Cl | F | —CH₃ |
| I-263 | Cl | Cl | Cl | F | —CH₂CH₃ |
| I-264 | Cl | Cl | Cl | F | —CH₂CH₂CH₃ |
| I-265 | Cl | Cl | Cl | F | —CH(CH₃)₂ |
| I-266 | Cl | Cl | Cl | F | —CH₂CH₂CH₂CH₃ |
| I-267 | Cl | Cl | Cl | F | —CH₂CH(CH₃)₂ |
| I-268 | Cl | Cl | Cl | F | —CH(CH₃)(CH₂CH₃) |
| I-269 | Cl | Cl | Cl | F | —C(CH₃)₃ |
| I-270 | Cl | Cl | Cl | F | (cyclopropylmethyl) |

TABLE 1-continued

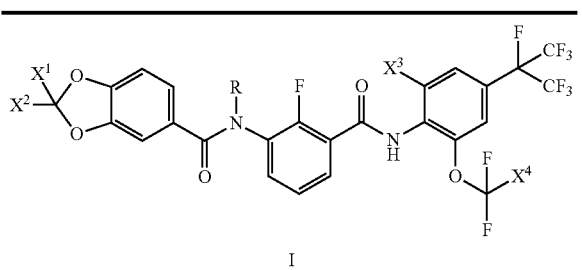

I

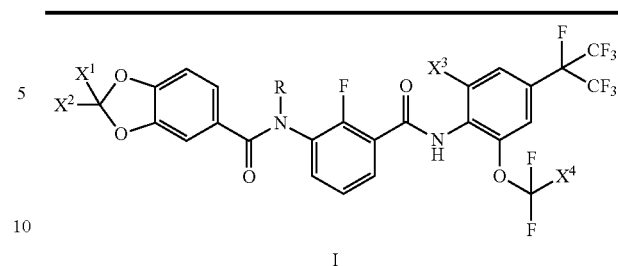

I

| No. | X¹ | X² | X³ | X⁴ | R |
|---|---|---|---|---|---|
| I-271 | Cl | Cl | Cl | F | —CH₂CH₂CH₂CH₂CH₃ |
| I-272 | Cl | Cl | Cl | F | —CH₂C(CH₃)₃ |
| I-273 | Cl | Cl | Cl | F | —CH₂CF₃ |
| I-274 | Cl | Cl | Cl | F | —CH₂CH₂CF₃ |
| I-275 | Cl | Cl | Cl | F | (structure) |
| I-276 | Cl | Cl | Cl | F | (structure) |
| I-277 | Cl | Cl | Cl | F | (structure) |
| I-278 | Cl | Cl | Cl | F | (structure) |
| I-279 | Cl | Cl | Cl | F | (structure) |
| I-280 | Cl | Cl | Cl | F | (structure) |
| I-281 | Cl | Cl | CF₃ | H | H |
| I-282 | Cl | Cl | CF₃ | H | —CH₃ |
| I-283 | Cl | Cl | CF₃ | H | —CH₂CH₃ |
| I-284 | Cl | Cl | CF₃ | H | —CH₂CH₂CH₃ |
| I-285 | Cl | Cl | CF₃ | H | —CH(CH₃)₂ |
| I-286 | Cl | Cl | CF₃ | H | —CH₂CH₂CH₂CH₃ |
| I-287 | Cl | Cl | CF₃ | H | —CH₂CH(CH₃)₂ |
| I-288 | Cl | Cl | CF₃ | H | —CH(CH₃)(CH₂CH₃) |
| I-289 | Cl | Cl | CF₃ | H | —C(CH₃)₃ |
| I-290 | Cl | Cl | CF₃ | H | (structure) |
| I-291 | Cl | Cl | CF₃ | H | —CH₂CH₂CH₂CH₂CH₃ |
| I-292 | Cl | Cl | CF₃ | H | —CH₂C(CH₃)₃ |
| I-293 | Cl | Cl | CF₃ | H | —CH₂CF₃ |
| I-294 | Cl | Cl | CF₃ | H | —CH₂CH₂CF₃ |
| I-295 | Cl | Cl | CF₃ | H | (structure) |
| I-296 | Cl | Cl | CF₃ | H | (structure) |
| I-297 | Cl | Cl | CF₃ | H | (structure) |
| I-298 | Cl | Cl | CF₃ | H | (structure) |
| I-299 | Cl | Cl | CF₃ | H | (structure) |
| I-300 | Cl | Cl | CF₃ | H | (structure) |
| I-301 | Cl | Cl | CF₃ | F | H |
| I-302 | Cl | Cl | CF₃ | F | —CH₃ |
| I-303 | Cl | Cl | CF₃ | F | —CH₂CH₃ |
| I-304 | Cl | Cl | CF₃ | F | —CH₂CH₂CH₃ |
| I-305 | Cl | Cl | CF₃ | F | —CH(CH₃)₂ |
| I-306 | Cl | Cl | CF₃ | F | —CH₂CH₂CH₂CH₃ |
| I-307 | Cl | Cl | CF₃ | F | —CH₂CH(CH₃)₂ |
| I-308 | Cl | Cl | CF₃ | F | —CH(CH₃)(CH₂CH₃) |
| I-309 | Cl | Cl | CF₃ | F | —C(CH₃)₃ |
| I-310 | Cl | Cl | CF₃ | F | (structure) |
| I-311 | Cl | Cl | CF₃ | F | —CH₂CH₂CH₂CH₂CH₃ |
| I-312 | Cl | Cl | CF₃ | F | —CH₂C(CH₃)₃ |
| I-313 | Cl | Cl | CF₃ | F | —CH₂CF₃ |
| I-314 | Cl | Cl | CF₃ | F | —CH₂CH₂CF₃ |
| I-315 | Cl | Cl | CF₃ | F | (structure) |
| I-316 | Cl | Cl | CF₃ | F | (structure) |
| I-317 | Cl | Cl | CF₃ | F | (structure) |

TABLE 1-continued

Structure I: benzodioxole-CX¹X²-O linked to benzamide with R,F substituents, linked via NH to phenyl with X³, CF₃/CF₃, and OCF₂X⁴ group.

| No. | X¹ | X² | X³ | X⁴ | R |
|---|---|---|---|---|---|
| I-318 | Cl | Cl | CF₃ | F | (geranyl group: CH₂-CH=C(CH₃)-CH₂-CH₂-CH=C(CH₃)₂) |
| I-319 | Cl | Cl | CF₃ | F | -(CH₂)₃-O-CH₃ |
| I-320 | Cl | Cl | CF₃ | F | -(CH₂)₃-S-CH₃ |
| I-321 | F | H | Br | H | H |
| I-322 | F | H | Br | H | —CH₃ |
| I-323 | F | H | Br | H | —CH₂CH₃ |
| I-324 | F | H | Br | F | H |
| I-325 | F | H | Br | F | —CH₃ |
| I-326 | F | H | Br | F | —CH₂CH₃ |
| I-327 | F | H | Cl | H | H |
| I-328 | F | H | Cl | H | —CH₃ |
| I-329 | F | H | Cl | F | H |
| I-330 | F | H | Cl | F | —CH₃ |
| I-331 | F | H | F | H | H |
| I-332 | F | H | F | F | H |
| I-333 | F | H | I | H | H |
| I-334 | F | H | I | H | —CH₃ |
| I-335 | F | H | I | F | H |
| I-336 | F | H | I | F | —CH₃ |
| I-337 | Br | Br | Br | H | H |
| I-338 | Br | Br | Br | H | —CH₃ |
| I-339 | Br | Br | Br | H | —CH₂CH₃ |
| I-340 | Br | Br | Br | F | H |
| I-341 | Br | Br | Br | F | —CH₃ |
| I-342 | Br | Br | Br | F | —CH₂CH₃ |
| I-343 | Br | Br | Cl | H | H |
| I-344 | Br | Br | Cl | H | —CH₃ |
| I-345 | Br | Br | Cl | F | H |
| I-346 | Br | Br | Cl | F | —CH₃ |
| I-347 | Br | Br | F | H | H |
| I-348 | Br | Br | F | F | H |
| I-349 | Br | Br | I | H | H |
| I-350 | Br | Br | I | H | —CH₃ |
| I-351 | Br | Br | I | F | H |
| I-352 | Br | Br | I | F | —CH₃ |
| I-353 | I | I | Br | H | H |
| I-354 | I | I | Br | H | —CH₃ |
| I-355 | I | I | Br | H | —CH₂CH₃ |
| I-356 | I | I | Br | F | H |
| I-357 | I | I | Br | F | —CH₃ |
| I-358 | I | I | Br | F | —CH₂CH₃ |
| I-359 | I | I | Cl | H | H |
| I-360 | I | I | Cl | H | —CH₃ |
| I-361 | I | I | Cl | F | H |
| I-362 | I | I | Cl | F | —CH₃ |
| I-363 | I | I | F | H | H |
| I-364 | I | I | F | F | H |
| I-365 | I | I | I | H | H |
| I-366 | I | I | I | H | —CH₃ |
| I-367 | I | I | I | F | H |
| I-368 | I | I | I | F | —CH₃ |

¹H NMR (600 MHz, CDCl₃, ppm) and physicochemical properties of some compounds are as follows:

| Compound | Nuclear Magnetic Data | Physical Property |
|---|---|---|
| I-1 | 8.60 (t, 1H), 8.04-7.98 (m, 3H), 7.87 (t, 1H), 7.70-7.68 (m, 2H), 7.53 (s, 1H), 7.39 (t, 1H), 7.22 (d, 1H), 6.58 (t, 1H). | White solid |
| I-2 | 8.03 (t, 1H), 7.99 (d, 1H), 7.91 (d, 1H), 7.51 (s, 1H), 7.45 (t, 1H), 7.31 (t, 1H), 7.21 (s, 1H), 7.04 (s, br, 1H), 6.89 (d, br, 1H), 6.52 (t, 1H), 3.49 (s, 3H). | White solid |
| I-41 | 8.60 (t, 1H), 8.07-8.03 (m, 2H), 7.86 (t, 1H), 7.81 (s, 1H), 7.69-7.68 (m, 2H), 7.52 (s, 1H), 7.38 (t, 1H), 7.21 (d, 1H), 6.61 (t, 1H). | White solid |
| I-42 | 8.03 (t, 1H), 7.96 (d, 1H), 7.80 (d, 1H), 7.50 (s, 1H), 7.43 (t, 1H), 7.31 (t, 1H), 7.20 (s, 1H), 7.05 (s, br, 1H), 6.89 (d, br, 1H), 6.55 (t, 1H), 3.48 (s, 3H). | White solid |
| I-43 | 8.03 (t, 1H), 7.94 (d, 1H), 7.79 (d, 1H), 7.49(s, 1H), 7.44 (t, 1H), 7.32 (t, 1H), 7.19 (s, 1H), 7.03 (s, br, 1H), 6.87 (s, br, 1H), 6.55 (t, 1H), 3.99-3.93 (m, br, 2H), 1.27 (t, 3H). | White solid |
| I-44 | 8.02 (t, 1H), 7.94 (d, 1H), 7.79 (d, 1H), 7.49 (s, 1H), 7.45 (t, 1H), 7.32 (t, 1H), 7.18 (s, 1H), 7.01 (s, br, 1H), 6.87 (d, br, 1H), 6.55 (t, 1H), , 3.84 (s, br, 2H) , 1.68 (s, br, 1H), 0.98 (s, br, 3H). | Pale yellow solid |
| I-46 | 8.03 (t, 1H), 7.94 (d, 1H), 7.79 (s, 1H), 7.49 (s, 1H), 7.46 (t, 1H), 7.32 (t, 1H), 7.18 (s, 1H), 7.01 (s, br, 1H), 6.86 (s, br, 1H), 6.55 (t, 1H), 3.88 (t, br, 2H), 1.65-1.62 (m, br, 2H), 1.41-1.38 (m, br, 2H), 0.95 (t, 3H). | Pale yellow solid |
| I-47 | 8.01 (t, 1H), 7.89 (s, br, 1H), 7.79 (s, 1H), 7.49 (s, br, 2H), 7.32 (t, 1H), 7.17 (s, 1H), 6.98 (s, br, 1H), 6.85 (s, br, 1H), 6.54 (t, 1H), 3.84-3.73 (m, br, 2H), 1.94 (s, br, 1H), 1.00 (s, br, 6H). | Pale yellow solid |
| I-50 | 8.04 (t, 1H), 7.95 (d, 1H), 7.79 (s, 1H), 7.52-7.49 (m, 2H), 7.32 (t, 1H), 7.20 (s, 1H), 7.05 (s, br, 1H), 6.87 (s, br, 1H), 6.55 (t, 1H), 3.84-3.73 (m, br, 2H), 1.09 (s, br, 1H), 0.50 (s, br, 2H), 0.14-0.19 (m, br, 2H). | White solid |
| I-57 | 8.03 (s, br, 1H), 7.92 (s, br, 1H), 7.79 (s, 1H), 7.49 (s, 1H), 7.45 (s, br, 1H), 7.32 (s, br, 1H), 7.18 (s, 1H), 7.00 (s, br, 1H), 6.85 (s, br, 1H), 6.55 (t, 1H), 5.06 (s, br, 1H), 3.90 (s, br, 2H), 1.99-1.93 (m, 2H), 1.69-1.19 (m, 11H), 0.94 (s, br, 3H). | Pale yellow solid |
| I-60 | 8.03 (t, 1H), 7.92 (d, 1H), 7.79 (d, 1H), 7.52-7.49 (m, 2H), 7.33 (t, 1H), 7.18 (s, 1H), 7.01 (s, br, 1H), 6.86 (s, br, 1H), 6.55 (t, 1H), 3.97 (s, br, 2H), 2.57 (s, br, 2H), 2.08 (s, 3H), 1.97 (s, br, 2H). | Pale yellow solid |
| I-62 | 8.04 (t, 1H), 7.94 (d, br, 1H), 7.87 (s, 1H), 7.56 (s, 1H), 7.46 (t, 1H), 7.32 (t, 1H), 7.20 (s, 1H), 7.03 (s, br, 1H), 6.88 (d, br, 1H), 3.49 (s, 3H). | White solid |
| I-81 | 8.60 (t, 1H), 8.06-8.01 (m, 2H), 7.87 (t, 1H), 7.69-7.68 (m, 2H), 7.65 (s, 1H), 7.48 (s, 1H), 7.39 (t, 1H), 7.22 (d, 1H), 6.62 (t, 1H). | White solid |
| I-82 | 8.02 (t, 1H), 7.98 (d, 1H), 7.64 (s, 1H), 7.45 (s, 1H), 7.42 (t, 1H), 7.30 (t, 1H), 7.20 (s, 1H), 7.05 (s, br, 1H), 6.90 (d, br, 1H), 6.56 (t, 1H), 3.48 (s, 3H). | White solid |
| I-121 | 8.60 (t, 1H), 8.14 (d, 1H), 8.03 (s, br, 1H), 7.85-7.83 (m, 2H), 7.78 (s, 1H), 7.69-7.68 (m, 2H), 7.38 (t, 1H), 7.22 (d, 1H), 6.62 (t, 1H). | White solid |
| I-122 | 8.05-8.00 (m, 2H), 7.82 (s, 1H), 7.75 (s, 1H), 7.47 (t, 1H), 7.32 (t, 1H), 7.20 (s, 1H), 7.01 (s, br, 1H), 6.87 (d, br, 1H), 6.56 (t, 1H), 3.49 (s, 3H). | White solid |

In organic molecules, due to the difference in electronegativity, volume or spatial configuration of the substituents, the entire molecule may have a great difference in the transport properties or binding to the receptors in organisms such as insects and plants, and may also show a great difference in biological activity. The transport properties and suitability for binding to the receptors in the molecule are unpredictable and can be known by a lot of creative labor.

Compared with the compounds $KC_1$, $KC_2$, $KC_3$, $KC_4$ and MC, the piperonylic acid derivative (the compound of the general formula I) of the present invention shows unexpected high insecticidal activity and high acaricidal activity, and can control the following pests: lepidopteran pests such as armyworm, beet armyworm and diamondback moth; homopteran pests such as green peach aphid, leaf hopper and plant hopper; hemipteran pests such as corn chinch bug, tomato fleahopper and rice skunk; thysanoptera pests such as western flower thrips, *Thrips tabaci* lindemen, alfalfa thrips and soybean thrips; coleoptera pests such as potato beetles and elateridae; diptera pests such as flies and mosquitoes; hymenoptera pests such as bees and ants. The piperonylic acid derivative can control the following mites: tetranychidae (*Tetranychus urticae* koch, *Tetranychus cinnabarinus*, *Panonychus ulmi* and *Panonychus citri*), eriophyidae and tarsonemidae. Therefore, the present invention also comprises a purpose of the compound of the general formula I for controlling pests and mites in the fields of agriculture, forestry and sanitation.

The present invention also comprises an insecticidal and acaricidal composition which comprises the compound shown in the above general formula I and an acceptable carrier in the field of agriculture, forestry or sanitation. The compound shown in the general formula I is taken as an active component, and the weight percentage content of the active component in the composition is 1-99%. The composition may include the compound shown in the above general formula I in the existence form of the isomer structures.

The composition may be used in the form of dry powder, wettable powder, an emulsifiable concentrate, a microemulsion, a paste, a granule, a solution, a suspending agent, etc., and the selection of the type of the composition depends on the specific application.

The composition is prepared in a known manner, for example by diluting or dissolving the active substance with a solvent medium and/or a solid diluent, optionally in the presence of a surfactant.

An available solid diluent or carrier can be silica, kaolin, bentonite, talc, diatomite, dolomite, calcium carbonate, magnesia, chalk, clay, synthetic silicate, attapulgite, sepiolite, etc.

In addition to water, available liquid diluents are aromatic organic solvents (a mixture of xylene or alkylbenzene, chlorobenzene, etc.), paraffins (petroleum fractions), alcohols (methanol, propanol, butanol, octanol and glycerol), esters (ethyl acetate and isobutyl acetate), ketones (cyclohexanone, acetone, acetophenone, isophorone and ethyl amyl ketone) and amides (N, N-dimethylformamide and N-methylpyrrolidone).

Available surfactants are alkyl sulfonate, alkylaryl sulfonate, alkylphenol ethoxylate, polyoxyethylene sorbitan fatty acid ester and lignosulfonate.

The composition can also comprise special additives for specific purposes such as binders, e.g. gum arabic, polyvinyl alcohol and polyvinylpyrrolidone.

The concentration of the active component in the above composition may vary within a wide range according to the active component, the use objective, environmental conditions and the type of the adopted preparation. Generally, the concentration range of the active component is 1-90%, preferably 5-50%.

The technical solution of the present invention also comprises a method for controlling pests: applying the insecticidal composition of the present invention to a pest or a growth medium of the pest. The more appropriate effective dose which is often selected is 10 to 1000 grams per hectare, and preferably, the effective dose is 20 to 500 grams per hectare.

The technical solution of the present invention also comprises a method for controlling mites: applying the insecticidal composition of the present invention to a mite or a growth medium of the mite. The more appropriate effective dose which is often selected is 10 to 1000 grams per hectare, and preferably, the effective dose is 20 to 500 grams per hectare.

For some applications, for example in agriculture, the addition of one or more other fungicides, insecticides, acaricides, herbicides, plant growth regulators or fertilizers to the insecticidal, acaricidal and fungicidal composition of the present invention can produce additional advantages and effects.

It should be understood that various modifications and changes can be made within the scope limited by claims of the present invention.

The present invention has the following advantages:

In the present invention, the compound of the general formula I is obtained by introducing piperonylic acid natural active molecules and 2-halomethoxy-substituted-4-heptafluoroisopropyl aniline active substructure. Compared with $KC_4$ and MC, as well as $KC_1$ and $KC_2$, the molecular structure of the compound of the general formula I is obviously different. These differences lead to changes in the opportunities for molecules to interact with and bind to receptors, and obtain unexpected effects. Namely, the compound of the general formula I shows excellent killing activity against a variety of pests and mites, and also exhibits unexpected good control effect on thylanoptera pests, such as *Frankliniella occidentalis*, which is difficult to manage in the world. Therefore, the compound of the general formula I has important practical application value.

DETAILED DESCRIPTION

The following specific embodiments are used to further illustrate the present invention, but the present invention is not limited to these examples.

SYNTHESIS EMBODIMENTS

Embodiment 1: Preparation of Compound I-42

1) Preparation of N-(2-bromo-6-difluoromethoxy-4-heptafluoroisopropyl phenyl)-2-fluoro-3-nitrobenzamide

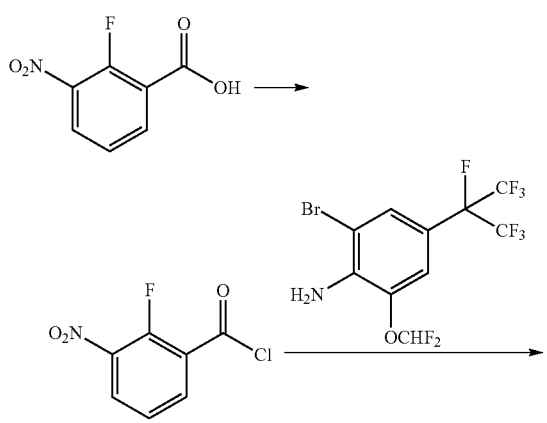

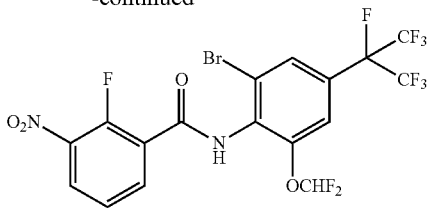

2-fluoro-3-nitrobenzoic acid (3.71 g, 20.0 mmol), thionyl chloride (16.05 g) and DMF (0.20 g) were added to a reaction flask. The reaction mixture was heated to 80° C. to react for 6 hours, and decompressed to distill off thionyl chloride. The obtained acyl chloride was dissolved in acetonitrile (40 mL), and then 2-bromo-6-difluoromethoxy-4-heptafluoroisopropylaniline (4.06 g, 10.0 mmol) and potassium iodide (0.42 g) were added. The resulting mixture was heated to 85° C. to react. After the reaction was complete by Thin-Layer Chromatography monitoring, taking about 12 hours, the reaction solution was cooled to room temperature, filtered to remove insolubles, and decompressed to distill off acetonitrile. Ethyl acetate (30 mL) was added to dissolve the residue. The solution was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silia gel to obtain 5.32 g of the target compound as a white solid, with 92% yield (calculated based on the 2-bromo-6-difluoromethoxy-4-heptafluoroisopropylaniline).

$^1$H NMR (600 MHz, CDCl$_3$, ppm): 8.42 (t, 1H), 8.28 (t, 1H), 8.12 (d, 1H), 7.82 (s, 1H), 7.52-7.50 (m, 2H), 6.60 (t, 1H).

2) Preparation of N-(2-bromo-6-difluoromethoxy-4-heptafluoroisopropyl phenyl)-2-fluoro-3-aminobenzamide

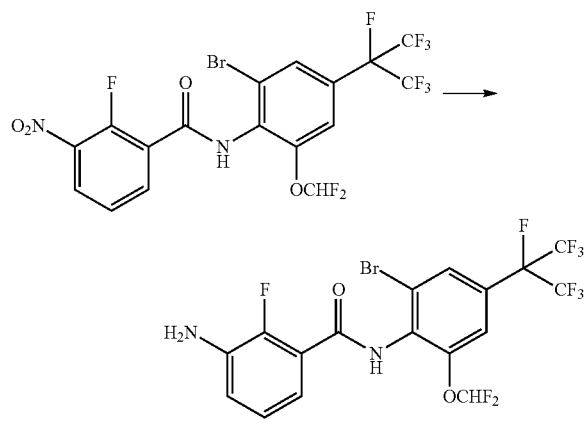

To a reaction flask N-(2-bromo-6-difluoromethoxy-4-heptafluoroisopropyl phenyl)-2-fluoro-3-nitrobenzamide (2.89 g, 5.0 mmol), dioxane (20 mL) and stannous chloride (4.60 g, 20.0 mmol) were added, and then concentrated hydrochloric acid (4 mL) was slowly added dropwise. The reaction mixture was heated to 60-65° C. to react. After the reaction was complete by Thin-Layer Chromatography monitoring, the mixture was cooled to room temperature, and then poured into ice water (30 mL). Ethyl acetate (50 mL) was added. Sodium hydroxide was slowly added to neutralize to pH=8-9. After the resulting mixture with precipitate was filtered through diatomite, the filter cake was washed with ethyl acetate and the filtrate was layered. The organic phase was dried over anhydrous magnesium sulfate and decompressed to distill off organic solvents. The residue was purified by column chromatography on silica gel to obtain 2.56 g of the target compound as a yellow solid, with 93% yield.

$^1$H NMR (600 MHz, CDCl$_3$, ppm): 8.14 (d, 1H), 7.79 (s, 1H), 7.51 (s, 1H), 7.45 (t, 1H), 7.09 (t, 1H), 7.00 (t, 1H), 6.60 (t, 1H), 3.93 (s, br, 2H).

3) Preparation of N-(2-bromo-6-difluoromethoxy-4-heptafluoroisopropyl phenyl)-2-fluoro-3-(methylamino)benzamide

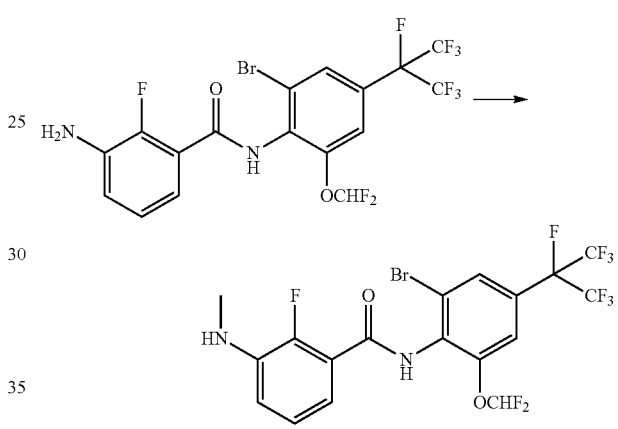

Concentrated sulfuric acid (3 mL) and N-(2-bromo-6-difluoromethoxy-4-heptafluoroisopropyl phenyl)-2-fluoro-3-aminobenzamide (0.55 g, 1.0 mmol) were added to a reaction flask, and fully stirred for dissolving. Aqueous formaldehyde solution (2 mL) was slowly added dropwise at 30-35° C., and then the temperature was increased to 40° C. to continue the reaction. After the reaction was complete by Thin-Layer Chromatography monitoring, the reaction mixture was cooled to room temperature, and slowly poured into ice water (10 mL), and fully stirred. The solid was precipitated, and filtered, and the filter cake was purified by column chromatography on silica gel to obtain 0.51 g of the target compound as a white solid, with 90% yield.

$^1$H NMR (600 MHz, CDCl$_3$, ppm): 8.13 (d, 1H), 7.79 (s, 1H), 7.51 (s, 1H), 7.35 (t, 1H), 7.17 (t, 1H), 6.89 (t, 1H), 6.60 (t, 1H), 4.14 (s, br, 1H), 2.94 (s, 3H).

4) Preparation of N-(2-bromo-6-difluoromethoxy-4-heptafluoroisopropyl phenyl)-2-fluoro-3-(N-methyl-2,2-difluoro-1,3-benzodioxole-5-carboxamido) benzamide (Compound I-42)

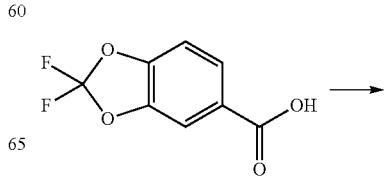

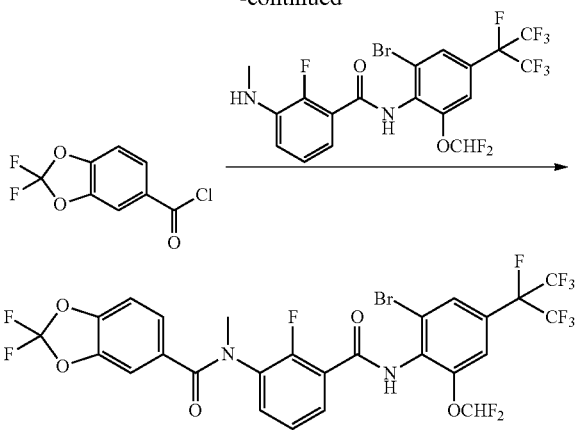

2,2-difluoro-1,3-benzodioxole-5-carboxylic acid (0.21 g, 1.0 mmol), thionyl chloride (1.01 g), toluene (10 mL) and DMF (1 drop) were added to a reaction flask. The reaction mixture was heated to 80° C. to react for 4 hours, and decompressed to distill off thionyl chloride. The acyl chloride obtained was dissolved in toluene (20 mL), and then N-(2-bromo-6-difluoromethoxy-4-heptafluoroisopropylphenyl)-2-fluoro-3-methylaminobenzamide (0.50 g, 0.89 mmol) was added. The resulting mixture was heated to 110° C. to react. After the reaction was complete by Thin-Layer Chromatography monitoring, the reaction mixture was cooled to room temperature, and fully stirred. The solid was gradually precipitated, and filtered. The filter cake was purified by column chromatography on silica gel to obtain 0.57 g of the target compound as a white solid, with 85% yield (calculated based on the N-(2-bromo-6-difluoromethoxy-4-heptafluoroisopropylphenyl)-2-fluoro-3-methylaminobenzamide).

$^1$H NMR (600 MHz, CDCl$_3$, ppm): 8.03 (t, 1H), 7.96 (d, 1H), 7.80 (d, 1H), 7.50 (s, 1H), 7.43 (t, 1H), 7.31 (t, 1H), 7.20 (s, 1H), 7.05 (s, br, 1H), 6.89 (d, br, 1H), 6.55 (t, 1H), 3.48 (s, 3H).

Embodiment 2: Preparation of Compound I-41

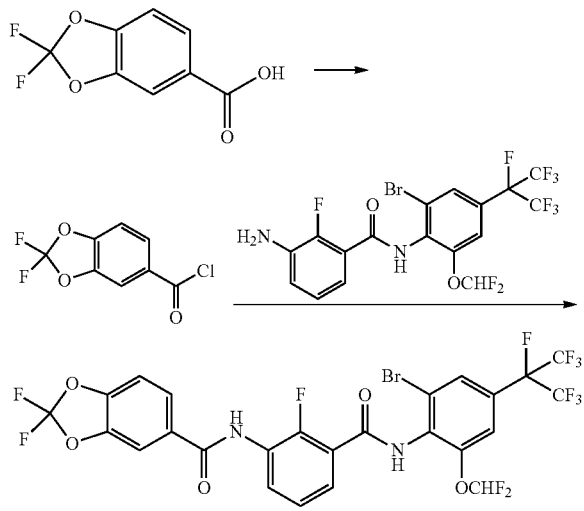

2,2-difluoro-1,3-benzodioxole-5-carboxylic acid (0.21 g, 1.0 mmol), thionyl chloride (1.06 g), toluene (10 mL) and DMF (1 drop) were added to a reaction flask. The reaction mixture was heated to 80° C. to react for 4 hours, and decompressed to distill off thionyl chloride. The acyl chloride obtained was dissolved in toluene (20 mL), and then N-(2-bromo-6-difluoromethoxy-4-heptafluoroisopropylphenyl)-2-fluoro-3-aminobenzamide (0.50 g, 0.9 mmol) was added. The resulting mixture was heated to 110° C. to react. After the reaction was complete by Thin-Layer Chromatography monitoring, the reaction mixture was cooled to room temperature, and fully stirred. The solid was gradually precipitated, and filtered. The filter cake was purified by column chromatography on silica gel to obtain 0.52 g of the target compound as a white solid, with 78% yield (calculated based on the N-(2-bromo-6-difluoromethoxy-4-heptafluoroisopropylphenyl)-2-fluoro-3-aminobenzamide).

$^1$H NMR (600 MHz, CDCl$_3$, ppm): 8.60 (t, 1H), 8.07-8.03 (m, 2H), 7.86 (t, 1H), 7.81 (s, 1H), 7.69-7.68 (m, 2H), 7.52 (s, 1H), 7.38 (t, 1H), 7.21 (d, 1H), 6.61 (t, 1H).

Embodiment 3: Preparation of Compound I-43

1) Preparation of N-(2-bromo-6-difluoromethoxy-4-heptafluoroisopropyl phenyl)-2-fluoro-3-ethylaminobenzamide

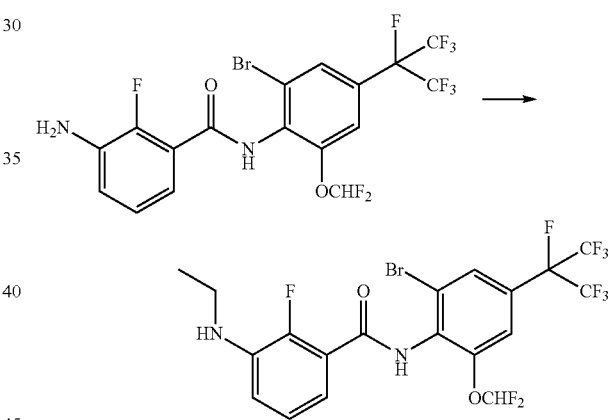

N-(2-bromo-6-difluoromethoxy-4-heptafluoroisopropylphenyl)-2-fluoro-3-aminobenzamide (2.20 g, 4.0 mmol), 40% acetaldehyde aqueous solution (0.67 g, 6.0 mmol), acetic acid (0.2 mL) and methanol (20 mL) were added to a reaction flask, and fully stirred for dissolving, and sodium cyanoborohydride (0.39 g, 6.0 mmol) was slowly added pinch by pinch at 25-30° C., and then the reaction mixture was stirred at room temperature to react. After the reaction was complete by Thin-Layer Chromatography monitoring, the reaction mixture was decompressed to distill off methanol, and ethyl acetate (30 mL) was added to dissolve. the resulting mixture was washed successively with 4M sodium hydroxide solution and a saturated salt solution to separate an organic phase. The organic phase was dried over anhydrous magnesium sulfate, filtered and decompressed to distill off organic solvents. The residue was purified by column chromatography on silica gel to obtain 2.12 g of the target compound as a white solid, with 91% yield.

$^1$H NMR (600 MHz, CDCl$_3$, ppm): 8.13 (d, 1H), 7.79 (s, 1H), 7.51 (s, 1H), 7.34 (t, 1H), 7.15 (t, 1H), 6.90 (t, 1H), 6.60 (t, 1H), 3.99 (s, br, 1H), 3.25 (q, 2H), 1.33 (t, 3H).

2) Preparation of N-(2-bromo-6-difluoromethoxy-4-heptafluoroisopropyl phenyl)-2-fluoro-3-(N-ethyl-2,2-difluoro-1,3-benzodioxole-5-carboxamido) benzamide (Compound I-43)

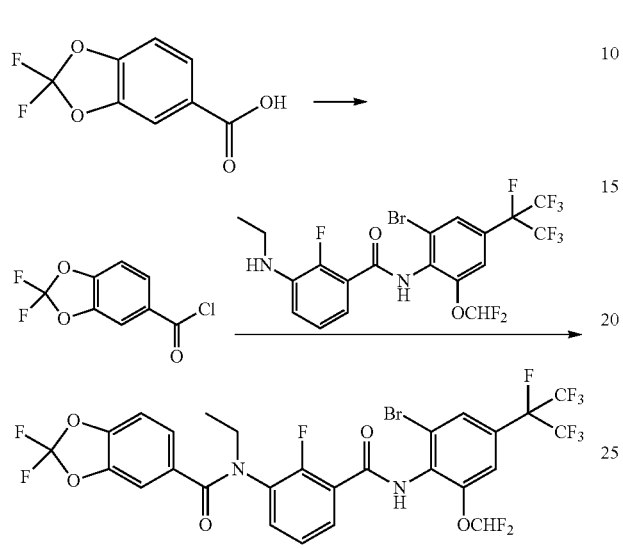

2,2-difluoro-1,3-benzodioxole-5-carboxylic acid (0.21 g, 1.0 mmol), thionyl chloride (1.01 g), toluene (10 mL) and DMF (1 drop) were added to a reaction flask. The reaction mixture was heated to 80° C. to react for 4 hours, and decompressed to distill off thionyl chloride. The obtained acyl chloride was dissolved in tetrahydrofuran (20 mL), and N-(2-bromo-6-difluoromethoxy-4-heptafluoroisopropylphenyl)-2-fluoro-3-ethylaminobenzamide (0.52 g, 0.9 mmol) was added. The reaction mixture was heated to 70° C. to react. After the reaction was complete by Thin-Layer Chromatography monitoring, the reaction mixture was cooled to room temperature, and decompressed to distill off tetrahydrofuran, and then ethyl acetate (30 mL) was added to dissolve. The resulting mixture was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silica gel to obtain 0.62 g of the target compound as a white solid, with 90% yield (calculated based on the N-(2-bromo-6-difluoromethoxy-4-heptafluoroisopropylphenyl)-2-fluoro-3-ethylaminobenzamide).

$^1$H NMR (600 MHz, CDCl$_3$, ppm): 8.03 (t, 1H), 7.94 (d, 1H), 7.79 (d, 1H), 7.49 (s, 1H), 7.44 (t, 1H), 7.32 (t, 1H), 7.19 (s, 1H), 7.03 (s, br, 1H), 6.87 (s, br, 1H), 6.55 (t, 1H), 3.99-3.93 (m, br, 2H), 1.27 (t, 3H).

Embodiment 4: Preparation of Compound I-46

1) Preparation of N-(2-bromo-6-difluoromethoxy-4-heptafluoroisopropyl phenyl)-2-fluoro-3-n-butylaminobenzamide

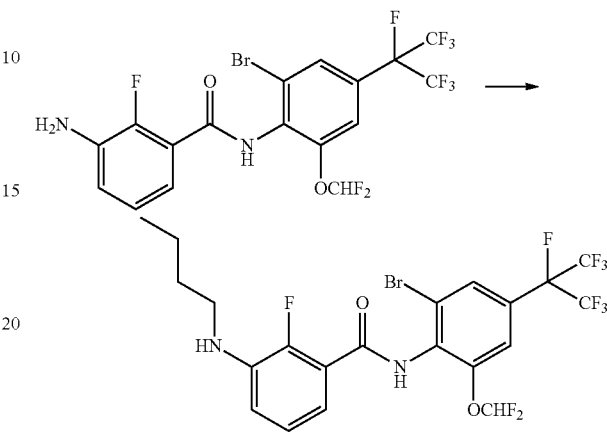

N-(2-bromo-6-difluoromethoxy-4-heptafluoroisopropylphenyl)-2-fluoro-3-aminobenzamide (2.20 g, 4.0 mmol), n-butyraldehyde (0.44 g, 6.0 mmol), acetic acid (0.2 mL) and methanol (20 mL) were added to a reaction flask, and fully stirred for dissolving, and sodium cyanoborohydride (0.39 g, 6.0 mmol) was slowly added pinch by pinch at 25-30° C., and then the reaction mixture was stirred at room temperature to react. After the reaction was complete by Thin-Layer Chromatography monitoring, the reaction mixture was decompressed to distill off methanol, and ethyl acetate (30 mL) was added to dissolve. the resulting mixture was washed successively with 4M sodium hydroxide solution and a saturated salt solution to separate an organic phase. The organic phase was dried over anhydrous magnesium sulfate, filtered and decompressed to distill off organic solvents. The residue was purified by column chromatography on silica gel to obtain 2.09 g of the target compound as a white solid, with 86% yield.

$^1$H NMR (600 MHz, CDCl$_3$, ppm): 8.13 (d, 1H), 7.79 (s, 1H), 7.51 (s, 1H), 7.32 (t, 1H), 7.14 (t, 1H), 6.90 (t, 1H), 6.60 (t, 1H), 4.04 (s, br, 1H), 3.19 (t, 2H), 1.70-1.65 (m, 2H), 1.50-1.44 (m, 2H), 0.99 (t, 3H).

2) Preparation of N-(2-bromo-6-difluoromethoxy-4-heptafluoroisopropyl phenyl)-2-fluoro-3-(N-n-butyl-2,2-difluoro-1,3-benzodioxole-5-carboxamido) benzamide (Compound I-46)

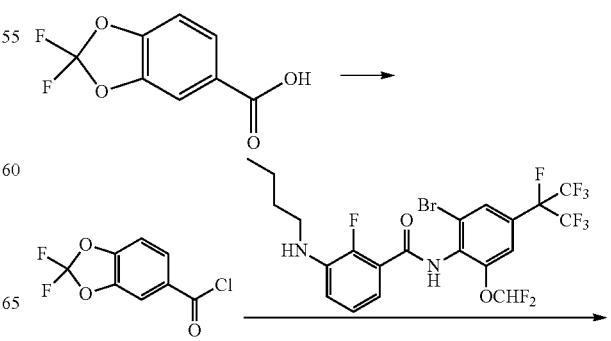

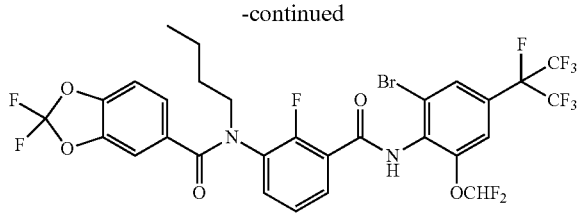

2,2-difluoro-1,3-benzodioxole-5-carboxylic acid (0.21 g, 1.0 mmol), thionyl chloride (1.01 g), toluene (10 mL) and DMF (1 drop) were added to a reaction flask. The reaction mixture was heated to 80° C. to react for 4 hours, and decompressed to distill off thionyl chloride. The obtained acyl chloride was dissolved in tetrahydrofuran (20 mL), and N-(2-bromo-6-difluoromethoxy-4-heptafluoroisopropylphenyl)-2-fluoro-3-n-butyl aminobenzamide (0.55 g, 0.9 mmol) was added. The reaction mixture was heated to 70° C. to react. After the reaction was complete by Thin-Layer Chromatography monitoring, the reaction mixture was cooled to room temperature, and decompressed to distill off tetrahydrofuran, and then ethyl acetate (30 mL) was added to dissolve. The resulting mixture was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silica gel to obtain 0.58 g of the target compound as a pale yellow solid, with 81% yield (calculated based on the N-(2-bromo-6-difluoromethoxy-4-heptafluoroisopropylphenyl)-2-fluoro-3-n-butylaminobenzamide).

$^1$H NMR (600 MHz, CDCl$_3$, ppm): 8.03 (t, 1H), 7.94 (d, 1H), 7.79 (s, 1H), 7.49 (s, 1H), 7.46 (t, 1H), 7.32 (t, 1H), 7.18 (s, 1H), 7.01 (s, br, 1H), 6.86 (s, br, 1H), 6.55 (t, 1H), 3.88 (t, br, 2H), 1.65-1.62 (m, br, 2H), 1.41-1.38 (m, br, 2H), 0.95 (t, 3H).

Embodiment 5: Preparation of Compound I-50

1) Preparation of N-(2-bromo-6-difluoromethoxy-4-heptafluoroisopropyl phenyl)-2-fluoro-3-(cyclopropylmethylamino)benzamide

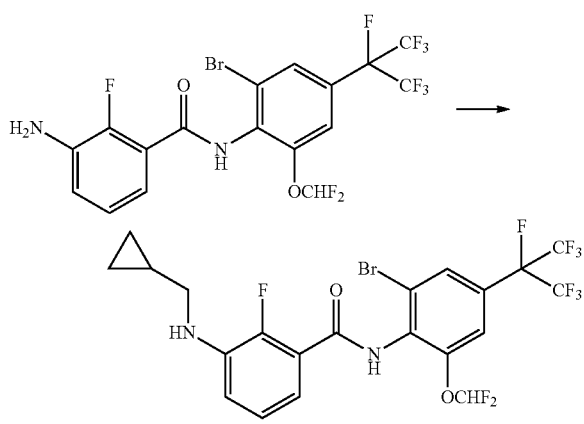

N-(2-bromo-6-difluoromethoxy-4-heptafluoroisopropylphenyl)-2-fluoro-3-aminobenzamide (2.20 g, 4.0 mmol), cyclopropanecarboxaldehyde (0.44 g, 6.0 mmol), acetic acid (0.2 mL) and methanol (20 mL) were added to a reaction flask, and fully stirred for dissolving, and sodium cyanoborohydride (0.39 g, 6.0 mmol) was slowly added pinch by pinch at 25-30° C., and then the reaction mixture was stirred at room temperature to react. After the reaction was complete by Thin-Layer Chromatography monitoring, the reaction mixture was decompressed to distill off methanol, and ethyl acetate (30 mL) was added to dissolve. the resulting mixture was washed successively with 4M sodium hydroxide solution and a saturated salt solution to separate an organic phase. The organic phase was dried over anhydrous magnesium sulfate, filtered and decompressed to distill off organic solvents. The residue was purified by column chromatography on silica gel to obtain 2.11 g of the target compound as a white solid, with 87% yield.

$^1$H NMR (600 MHz, CDCl$_3$, ppm): 8.15 (d, 1H), 7.79 (s, 1H), 7.51 (s, 1H), 7.33 (t, 1H), 7.13 (t, 1H), 6.88 (t, 1H), 6.60 (t, 1H), 4.21 (s, br, 1H), 3.04 (d, 2H), 1.18-1.12 (m, 1H), 0.63-0.60 (m, 2H), 0.31-0.28 (m, 2H).

2) Preparation of N-(2-bromo-6-difluoromethoxy-4-heptafluoroisopropyl phenyl)-2-fluoro-3-(N-cyclopropylmethyl-2,2-difluoro-1,3-benzodioxole-5-carboxamido) benzamide (Compound I-50)

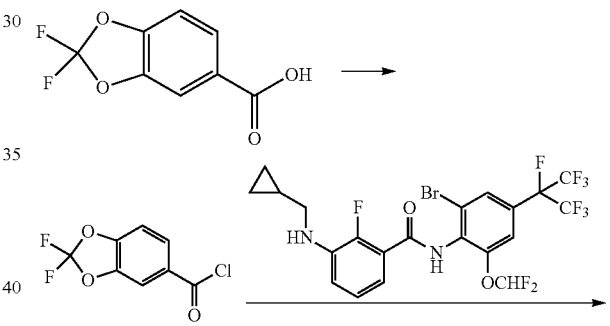

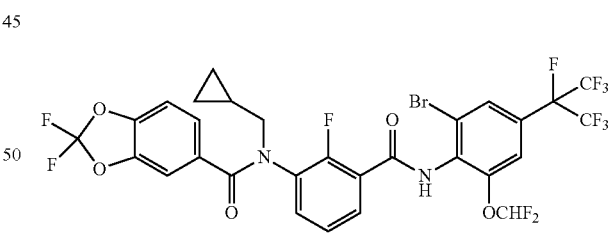

2,2-difluoro-1,3-benzodioxole-5-carboxylic acid (0.21 g, 1.0 mmol), thionyl chloride (1.01 g), toluene (10 mL) and DMF (1 drop) were added to a reaction flask. The reaction mixture was heated to 80° C. to react for 4 hours, and decompressed to distill off thionyl chloride. The obtained acyl chloride was dissolved in tetrahydrofuran (20 mL), and N-(2-bromo-6-difluoromethoxy-4-heptafluoroisopropylphenyl)-2-fluoro-3-cyclopropylmethylamino benzamide (0.54 g, 0.9 mmol) was added. The reaction mixture was heated to 70° C. to react. After the reaction was complete by Thin-Layer Chromatography monitoring, the reaction mixture was cooled to room temperature, and decompressed to distill off tetrahydrofuran, and then ethyl acetate (30 mL) was added to dissolve. The resulting mixture was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silica gel to obtain 0.57 g of the target compound as a white solid, with 80% yield (calculated based on the N-(2-bromo-6-difluoromethoxy-4-heptafluoroisopropylphenyl)-2-fluoro-3-(cyclopropylmethylamino)benzamide).

$^1$H NMR (600 MHz, CDCl$_3$, ppm): 8.04 (t, 1H), 7.95 (d, 1H), 7.79 (s, 1H), 7.52-7.49 (m, 2H), 7.32 (t, 1H), 7.20 (s, 1H), 7.05 (s, br, 1H), 6.87 (s, br, 1H), 6.55 (t, 1H), 3.84-3.73 (m, br, 2H), 1.09 (s, br, 1H), 0.50 (s, br, 2H), 0.14-0.19 (m, br, 2H).

Embodiment 6: Preparation of Compound I-60

1) Preparation of N-(2-bromo-6-difluoromethoxy-4-heptafluoroisopropyl phenyl)-2-fluoro-3-(3-methylthiopropylamino)benzamide

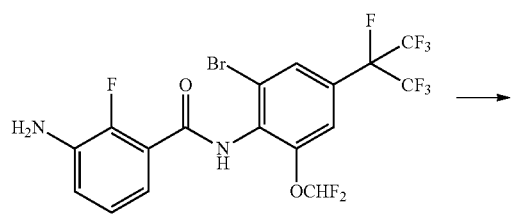

N-(2-bromo-6-difluoromethoxy-4-heptafluoroisopropylphenyl)-2-fluoro-3-aminobenzamide (2.20 g, 4.0 mmol), 3-methylthiopropanal (0.64 g, 6.0 mmol), acetic acid (0.2 mL) and methanol (20 mL) were added to a reaction flask, and fully stirred for dissolving, and sodium cyanoborohydride (0.39 g, 6.0 mmol) was slowly added pinch by pinch at 25-30° C., and then the reaction mixture was stirred at room temperature to react. After the reaction was complete by Thin-Layer Chromatography monitoring, the reaction mixture was decompressed to distill off methanol, and ethyl acetate (30 mL) was added to dissolve. the resulting mixture was washed successively with 4M sodium hydroxide solution and a saturated salt solution to separate an organic phase. The organic phase was dried over anhydrous magnesium sulfate, filtered and decompressed to distill off organic solvents. The residue was purified by column chromatography on silica gel to obtain 2.19 g of the target compound as a white solid, with 85% yield.

$^1$H NMR (600 MHz, CDCl$_3$, ppm): 8.13 (d, 1H), 7.79 (s, 1H), 7.51 (s, 1H), 7.34 (t, 1H), 7.15 (t, 1H), 6.93 (t, 1H), 6.60 (t, 1H), 4.19 (s, br, 1H), 3.35 (t, 2H), 2.65 (t, 2H), 2.14 (s, 3H), 2.00-1.95 (m, 2H).

2) Preparation of N-(2-bromo-6-difluoromethoxy-4-heptafluoroisopropyl phenyl)-2-fluoro-3-(N-(3-methylthiopropyl)-2,2-difluoro-1,3-benzodioxole-5-carboxamido) benzamide (Compound I-60)

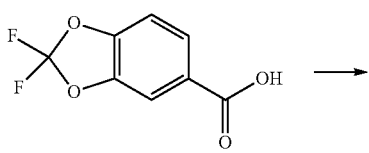

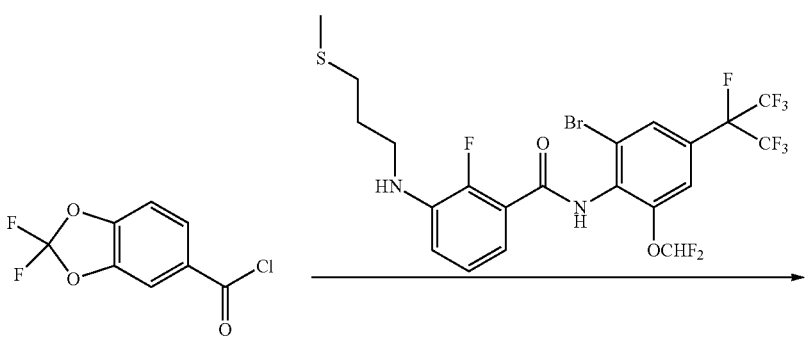

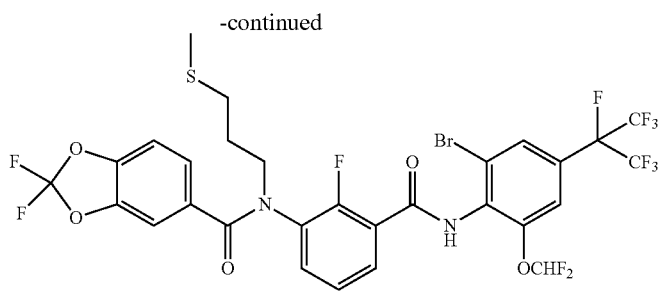

2,2-difluoro-1,3-benzodioxole-5-carboxylic acid (0.21 g, 1.0 mmol), thionyl chloride (1.01 g), toluene (10 mL) and DMF (1 drop) were added to a reaction flask. The reaction mixture was heated to 80° C. to react for 4 hours, and decompressed to distill off thionyl chloride. The obtained acyl chloride was dissolved in tetrahydrofuran (20 mL), and N-(2-bromo-6-difluoromethoxy-4-heptafluoroisopropylphenyl)-2-fluoro-3-(3-methylthiopropylamin o)benzamide (0.57 g, 0.9 mmol) was added. The reaction mixture was heated to 70° C. to react. After the reaction was complete by Thin-Layer Chromatography monitoring, the reaction mixture was cooled to room temperature, and decompressed to distill off tetrahydrofuran, and then ethyl acetate (30 mL) was added to dissolve. The resulting mixture was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silica gel to obtain 0.61 g of the target compound as a white solid, with 82% yield (calculated based on the N-(2-bromo-6-difluoromethoxy-4-heptafluoroisopropylphenyl)-2-fluoro-3-(3-methylthiopropylamin o)benzamide).

$^1$H NMR (600 MHz, CDCl$_3$, ppm): 8.03 (t, 1H), 7.92 (d, 1H), 7.79 (d, 1H), 7.52-7.49 (m, 2H), 7.33 (t, 1H), 7.18 (s, 1H), 7.01 (s, br, 1H), 6.86 (s, br, 1H), 6.55 (t, 1H), 3.97 (s, br, 2H), 2.57 (s, br, 2H), 2.08 (s, 3H), 1.97 (s, br, 2H).

Embodiment 7: Preparation of Compound I-81

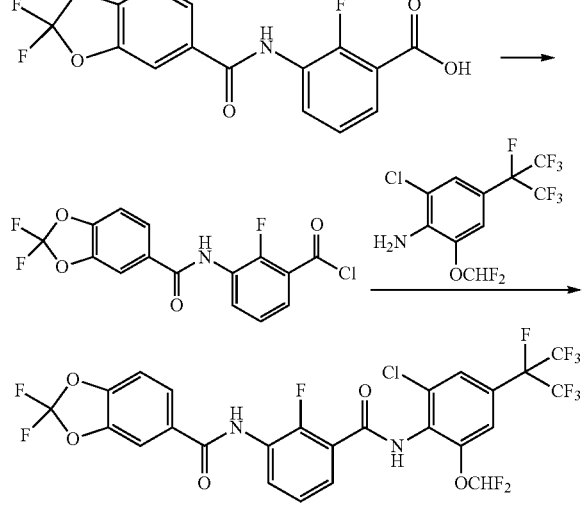

2-fluoro-3-(2,2-difluoro-1,3-benzodioxole-5-carboxamido) benzoic acid (CN109206397) (2.06 g, 6.0 mmol), thionyl chloride (3.60 g), toluene (10 mL) and DMF (1 drop) were added to a reaction flask. The reaction mixture was heated to 100° C. to react for 4 hours, and decompressed to distill off thionyl chloride and toluene. The obtained acyl chloride was dissolved in acetonitrile (15 mL), and 2-chloro-6-difluoromethoxy-4-heptafluoroisopropylaniline (1.46 g, 4.0 mmol) and potassium iodide (0.17 g, 1.0 mmol) were added. The reaction mixture was heated to reflux for 8 hours. The reaction mixture was cooled to room temperature, and ethyl acetate (30 mL) was added to dissolve. The resulting mixture was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silica gel to obtain 2.21 g of the target compound as a white solid, with 80% yield (calculated based on the 2-chloro-6-difluoromethoxy-4-heptafluoroisopropylaniline).

$^1$H NMR (600 MHz, CDCl$_3$, ppm): 8.60 (t, 1H), 8.06-8.01 (m, 2H), 7.87 (t, 1H), 7.69-7.68 (m, 2H), 7.65 (s, 1H), 7.48 (s, 1H), 7.39 (t, 1H), 7.22 (d, 1H), 6.62 (t, 1H).

Embodiment 8: Preparation of Compound I-2

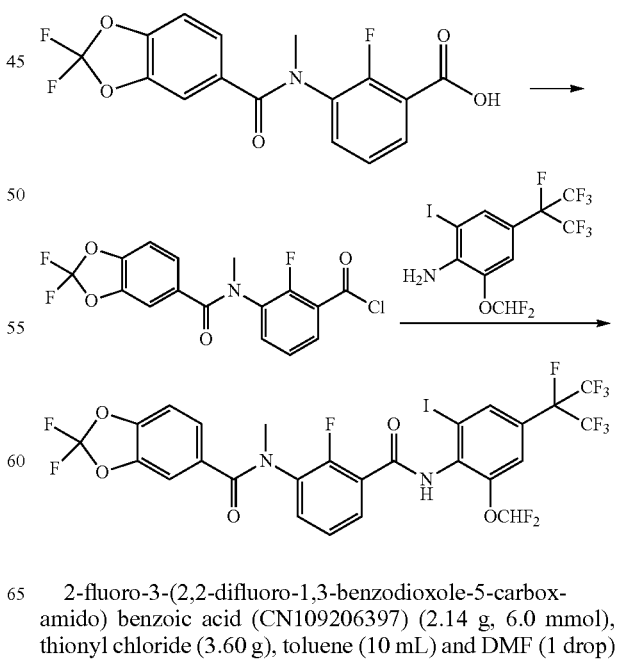

2-fluoro-3-(2,2-difluoro-1,3-benzodioxole-5-carboxamido) benzoic acid (CN109206397) (2.14 g, 6.0 mmol), thionyl chloride (3.60 g), toluene (10 mL) and DMF (1 drop)

were added to a reaction flask. The reaction mixture was heated to 100° C. to react for 6 hours, and decompressed to distill off thionyl chloride and toluene. The obtained acyl chloride was dissolved in acetonitrile (15 mL), and 2-difluoromethoxy-4-heptafluoroisopropyl-6-iodoaniline (1.83 g, 4.0 mmol) and potassium iodide (0.17 g, 1.0 mmol) were added. The reaction mixture was heated to reflux for 8 hours. The reaction mixture was cooled to room temperature, and ethyl acetate (30 mL) was added to dissolve. The resulting mixture was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silica gel to obtain 2.51 g of the target compound as a white solid, with 78% yield (calculated based on the 2-difluoromethoxy-4-heptafluoroisopropyl-6-iodoaniline).

$^1$H NMR (600 MHz, CDCl$_3$, ppm): 8.03 (t, 1H), 7.99 (d, 1H), 7.91 (d, 1H), 7.51 (s, 1H), 7.45 (t, 1H), 7.31 (t, 1H), 7.21 (s, 1H), 7.04 (s, br, 1H), 6.89 (d, br, 1H), 6.52 (t, 1H), 3.49 (s, 3H).

Embodiment 9: Preparation of Compound I-62

1) Preparation of N-(2-bromo-4-heptafluoroisopropyl-6-trifluoromethoxyphenyl)-2-fluoro-3-nitrobenzamide

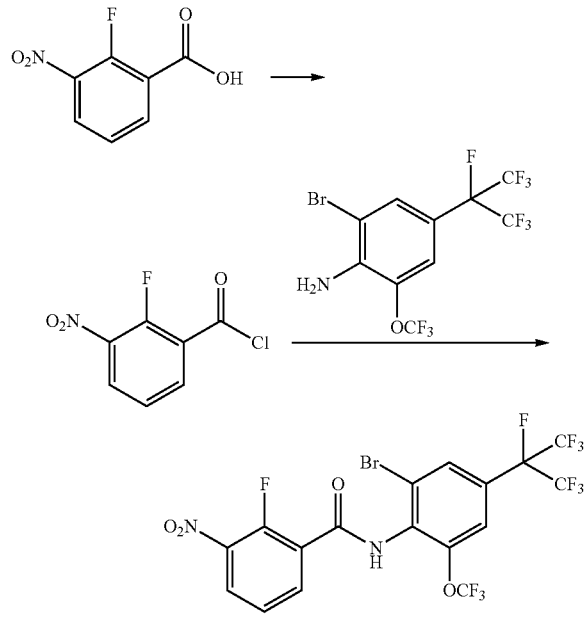

2-fluoro-3-nitrobenzoic acid (3.74 g, 20.0 mmol), thionyl chloride (16.05 g) and DMF (0.20 g) were added to a reaction flask. The reaction mixture was heated to 80° C. to react for 6 hours, and decompressed to distill off thionyl chloride. The obtained acyl chloride was dissolved in acetonitrile (40 mL), and then 2-bromo-4-heptafluoroisopropyl-6-trifluoromethoxyaniline (4.29 g, 10.0 mmol) and potassium iodide (0.42 g) were added. The resulting mixture was heated to 85° C. to react. After the reaction was complete by Thin-Layer Chromatography monitoring, taking about 12 hours, the reaction solution was cooled to room temperature, filtered to remove insolubles, and decompressed to distill off acetonitrile. Ethyl acetate (30 mL) was added to dissolve the residue. The solution was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silia gel to obtain 5.35 g of the target compound as a white solid, with 89% yield (calculated based on the 2-bromo-4-heptafluoroisopropyl-6-trifluoromethoxyaniline).

$^1$H NMR (600 MHz, CDCl$_3$, ppm): 8.44 (t, 1H), 8.29 (t, 1H), 8.08 (d, 1H), 7.89 (s, 1H), 7.60 (s, 1H), 7.53 (t, 1H).

2) Preparation of N-(2-bromo-4-heptafluoroisopropyl-6-trifluoromethoxyphenyl)-2-fluoro-3-aminobenzamide

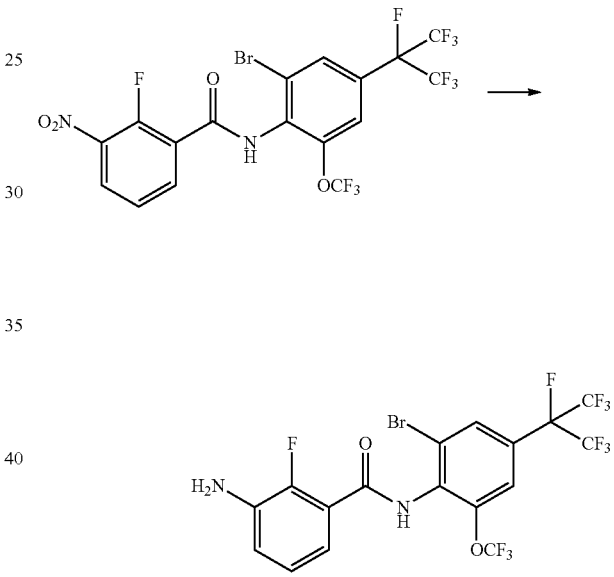

To a reaction flask N-(2-bromo-4-heptafluoroisopropyl-6-trifluoromethoxyphenyl)-2-fluoro-3-nitrobenzamide (2.99 g, 5 mmol), dioxane (20 mL) and stannous chloride (4.60 g, 20.0 mmol) were added, and then concentrated hydrochloric acid (4 mL) was slowly added dropwise. The reaction mixture was heated to 60-65° C. to react. After the reaction was complete by Thin-Layer Chromatography monitoring, the mixture was cooled to room temperature, and then poured into ice water (30 mL). Ethyl acetate (50 mL) was added. Sodium hydroxide was slowly added to neutralize to pH=8-9. After the resulting mixture with precipitate was filtered through diatomite, the filter cake was washed with ethyl acetate and the filtrate was layered. The organic phase was dried over anhydrous magnesium sulfate and decompressed to distill off organic solvents. The residue was purified by column chromatography on silica gel to obtain 2.66 g of the target compound as a yellow solid, with 93% yield.

$^1$H NMR (600 MHz, CDCl$_3$, ppm): 8.14 (d, 1H), 7.87 (s, 1H), 7.57 (s, 1H), 7.46 (t, 1H), 7.10 (t, 1H), 7.01 (t, 1H), 3.92 (s, br, 2H).

3) Preparation of N-(2-bromo-4-heptafluoroisopropyl-6-trifluoromethoxyphenyl)-2-fluoro-3-methylaminobenzamide

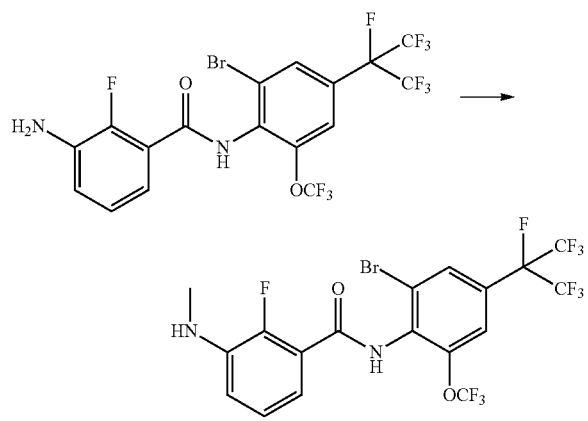

Concentrated sulfuric acid (3 mL) and N-(2-bromo-4-heptafluoroisopropyl-6-trifluoromethoxyphenyl)-2-fluoro-3-aminobenzamide (0.57 g, 1.0 mmol) were added to a reaction flask, and fully stirred for dissolving. Aqueous formaldehyde solution (2 mL) was slowly added dropwise at 30-35° C., and then the temperature was increased to 40° C. to continue the reaction. After the reaction was complete by Thin-Layer Chromatography monitoring, the reaction mixture was cooled to room temperature, and slowly poured into ice water (10 mL), and fully stirred. The solid was precipitated, and filtered, and the filter cake was purified by column chromatography on silica gel to obtain 0.52 g of the target compound as a white solid, with 89% yield.

$^1$H NMR (600 MHz, CDCl$_3$, ppm): 8.12 (d, 1H), 7.86 (s, 1H), 7.57 (s, 1H), 7.37 (t, 1H), 7.18 (t, 1H), 6.90 (t, 1H), 4.14 (s, br, 1H), 2.94 (s, 3H).

4) Preparation of N-(2-bromo-4-heptafluoroisopropyl-6-trifluoromethoxyphenyl)-2-fluoro-3-(N-methyl-2,2-difluoro-1,3-benzodioxole-5-carboxamido) benzamide (Compound I-62)

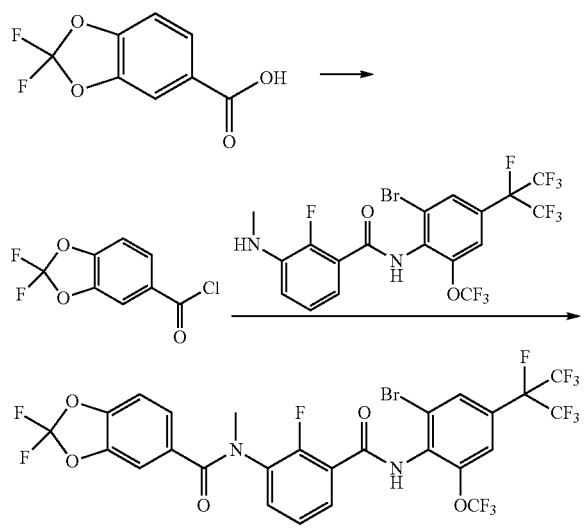

2,2-difluoro-1,3-benzodioxole-5-carboxylic acid (0.21 g, 1.0 mmol), thionyl chloride (1.01 g), toluene (10 mL) and DMF (1 drop) were added to a reaction flask. The reaction mixture was heated to 80° C. to react for 4 hours, and decompressed to distill off thionyl chloride. The acyl chloride obtained was dissolved in toluene (20 mL), and then N-(2-bromo-4-heptafluoroisopropyl-6-trifluoromethoxyphenyl)-2-fluoro-3-methylaminobenzamide (0.52 g, 0.9 mmol) was added. The resulting mixture was heated to 110° C. to react. After the reaction was complete by Thin-Layer Chromatography monitoring, the reaction mixture was cooled to room temperature, and fully stirred. The solid was gradually precipitated, and filtered. The filter cake was purified by column chromatography on silica gel to obtain 0.60 g of the target compound as a white solid, with 86% yield (calculated based on the N-(2-bromo-4-heptafluoroisopropyl-6-trifluoromethoxyphenyl)-2-fluoro-3-methylaminobenzamide).

$^1$H NMR (600 MHz, CDCl$_3$, ppm): 8.04 (t, 1H), 7.94 (d, br, 1H), 7.87 (s, 1H), 7.56 (s, 1H), 7.46 (t, 1H), 7.32 (t, 1H), 7.20 (s, 1H), 7.03 (s, br, 1H), 6.88 (d, br, 1H), 3.49 (s, 3H).

At the same time, other compounds shown in the general formula I can also be prepared in the manner described above.

Determination of Biological Activity

According to the solubility of test compounds, the compounds are dissolved with acetone or dimethyl sulfoxide, and then diluted with 0.1% Tween 80 solution to form a required concentration of 50 ml test liquid. The content of the acetone or the dimethyl sulfoxide in the total solution is not more than 10%.

Embodiment 10 Determination of Activity Against Armyworm

The middle leaves of fresh corns were cut into small sections of 3 cm, and dipped into a solution of the required concentration of test compounds for 10 seconds. After dried in shade, the middle leaves were placed in a 9 cm diameter petri dish provided with filter paper. Fourteen regular healthy test insects (third instar) were put into the leaves. Four replicates were set for each treatment. The pure water treatment was set as control check. The treated discs were placed in a chamber of 24° C., 60%-70% relative humidity and day light. After 72 hours, the number of surviving insects was investigated, and the mortality rate was calculated.

Among some of the testing compounds, compounds I-1, I-2, I-41, I-42, I-43, I-44, I-46, I-47, I-50, I-52, I-57, I-60, I-62, I-81, I-82, I-121 and I-122 showed over 90% mortality rates against armyworm at 10 mg/L.

Embodiment 11 Determination of Activity Against Diamondback Moth

The leaves of cabbage grown in greenhouse were selected, removed the surface waxy layers, punched into circular leaf discs with a diameter of 2 cm by using a puncher, and dipped into a solution of the required concentration of test compounds for 10 seconds. After dried in shade, the circular leaf discs were placed in a 9 cm diameter petri dish provided with filter paper. Ten regular healthy test insects (second instar) were put into the leaf discs. Four replicates were set for each treatment. The pure water treatment was set as control check. The treated discs were placed in a chamber of 24° C., 60%-70% relative humidity and day light. After 72 hours, the number of surviving insects was investigated, and the mortality rate was calculated.

Among some of the testing compounds, compounds I-1, I-2, I-41, I-42, I-43, I-44, I-46, I-47, I-50, I-52, I-57, I-60, I-62, I-81, I-82, I-121 and I-122 showed over 90% mortality rates against diamondback moth at 10 mg/L.

Embodiment 12 Determination of Activity Against Western Flower Thrips Nymphs

Fresh kidney bean leaves cultured in the glasshouse were selected and uniformly sprayed with 1 ml of the test liquid by using a handheld Airbrush. The leaves were dried naturally and placed in a test tube. Fifteen tidy and healthy western flower thrips nymphs were put into the leaves. Three replicates were set for each treatment. The water treatment was set as control check. After the treatment, the treated tube were placed in a chamber of 24° C., 60%-70% relative humidity and day light. After 72 hours, the number of surviving insects was investigated, and the mortality was calculated.

Part of test compounds: I-1, I-2, I-41, I-42, I-43, I-44, I-46, I-47, I-50, I-52, I-57, I-60, I-62, I-81, I-82, I-121 and I-122 showed over 90% mortality rates against western flower thrips nymphs at a concentration of 600 mg/L.

According to the above test method, compounds I-41 and I-42 as well as $KC_1$, $KC_2$, $KC_3$, $KC_4$ and MC were selected for parallel determination of activity against western flower thrips nymphs. See Table 1 for test results.

TABLE 1

Parallel Determination Results of Activity of Compounds I-41, I-42, $KC_1$, $KC_2$, $KC_3$, $KC_4$ and MC against Western Flower Thrips Nymphs (Mortality, %)

| Compound | Mortality (%) | |
|---|---|---|
| | 100 mg/L | 10 mg/L |
| Compound I-41 | 95 | 90 |
| Compound I-42 | 100 | 91 |
| $KC_1$ | 85 | 15 |
| $KC_2$ | 90 | 59 |
| $KC_3$ | 60 | 33 |
| $KC_4$ | 52 | 37 |
| MC | 76 | 72 |
| Cyantraniliprole | 85 | 25 |
| Spinetoram | 100 | 90 |

Embodiment 13 Determination of Acaricidal Activity

The adult spider mites were put into two true leaves of bean plants. After the number of mites was investigated, the solution of certain concentrations of test compounds was sprayed by using a handheld Airbrush. Three replicates were set for each treatment. Then the leaves were maintained in a standard observation room. After 72 hours, the number of surviving mites was investigated, and the mortality rate was calculated. Compounds I-41, $KC_3$, $KC_4$ and MC were selected for parallel determination of activity against *Tetranychus cinnabarinus* adults. See Table 2 for test results.

TABLE 2

Parallel Determination Results of Activity of Compounds I-41, $KC_3$, $KC_4$ and MC against *Tetranychus Cinnabarinus* Adult (Mortality, %)

| Compound | Mortality (%) | | |
|---|---|---|---|
| | 600 mg/L | 100 mg/L | 10 mg/L |
| Compound I-41 | 100 | 100 | 87 |
| $KC_3$ | 0 | 0 | 0 |
| $KC_4$ | 0 | 0 | 0 |
| MC | 0 | 0 | 0 |

Embodiment 14 Determination of *Tribolium confusum* Adults

The test liquid was prepared in the order from low dose to high dose according to the test design. Then, the liquid of different concentrations was added to feeding bran and uniformly stirred, and dried in the shade. Then, the resulting feeding bran was collected in a paper cup. Fifty *Tribolium confusum* adults with consistent size were put in the paper cup. Three replicates were set for each treatment. Control check was set. The treated test materials were put in an observation room under controlled conditions. After 72 h, the number of dead and surviving adults was investigated.

Part of test compounds: I-1, I-2, I-41, I-42, I-43, I-44, I-46, I-47, I-50, I-52, I-57, I-60, I-62, I-81, I-82, I-121 and I-122 showed over 90% mortality rates against *Tribolium confusum* adults at a concentration of 600 mg/L.

According to the above test method, compounds I-42 and I-44 as well as $KC_2$ and $KC_3$ were selected for parallel determination of activity against *Tribolium confusum* adults. See Table 3 for test results.

TABLE 3

Parallel Determination Results of Activity of Compounds I-42, I-44, $KC_2$ and $KC_3$ against *Tribolium Confusum* Adults (Mortality, %)

| Compound | Mortality (%) | |
|---|---|---|
| | 20 mg/L | 5 mg/L |
| Compound I-42 | 100 | 81 |
| Compound I-44 | 98 | 83 |
| $KC_2$ | 76 | 70 |
| $KC_3$ | 80 | 69 |
| Cyantraniliprole | 5 | 0 |

The invention claimed is:
1. A piperonylic acid derivative, of formula I:

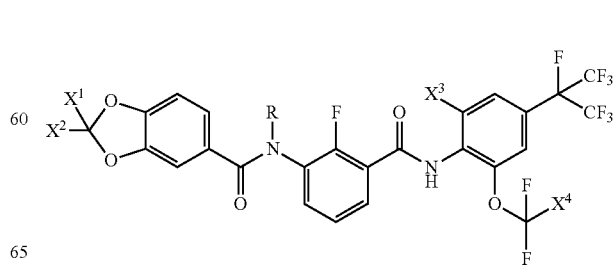

wherein:

$X^1$ is selected from halogens;

$X^2$ is selected from H and halogens;

$X^3$ is selected from halogens and $C_1$-$C_3$ haloalkyl;

$X^4$ is selected from H and halogens; and

R is selected from H, $C_1$-$C_6$ alkyl, $C_1$-$C_6$ haloalkyl, $C_2$-$C_{10}$ alkenyl, $C_1$-$C_6$ alkoxy $C_1$-$C_6$ alkyl, and $C_1$-$C_6$ alkylthio $C_1$-$C_6$ alkyl.

2. The piperonylic acid derivative according to claim 1, wherein:

$X^1$ is F, Cl, or Br;

$X^2$ is H, F, Cl, or Br;

$X^3$ is F, Cl, Br, I, or halomethyl; and $X^4$ is H, F, Cl, or Br.

3. The piperonylic acid derivative according to claim 2, wherein:

$X^1$ is F; and $X^2$ is H or F.

4. The piperonylic acid derivative according to claim 2, wherein $X^4$ is H or F.

5. The piperonylic acid derivative according to claim 2, wherein R is H, $C_1$-$C_6$ alkyl or methylthiopropyl.

6. A composition comprising the piperonylic acid derivative of claim 1 as an active component and a suitable carrier, wherein a weight percentage of the active component in the composition is 1-99%.

7. A method for controlling pests or mites, comprising applying the composition of claim 6 a pest, or a mite, or a growing medium at a dosage of 10 g to 1000 g per hectare.

* * * * *